US012672866B2

(12) United States Patent    (10) Patent No.:   US 12,672,866 B2

Carlo, III et al.    (45) Date of Patent:    Jul. 7, 2026

(54) SYNDESMOSIS DEVICE INSERTER

(71) Applicant: WRIGHT MEDICAL TECHNOLOGY, INC., Memphis, TN (US)

(72) Inventors: Robert Michael Carlo, III, Lakeland, TN (US); Vinay D. Patel, Memphis, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 62 days.

(21) Appl. No.: 18/671,198

(22) Filed: May 22, 2024

(65)      Prior Publication Data

US 2024/0389993 A1    Nov. 28, 2024

Related U.S. Application Data

(60) Provisional application No. 63/504,470, filed on May 26, 2023.

(51) Int. Cl.
    *A61B 17/04*       (2006.01)
    *A61B 17/68*       (2006.01)
(52) U.S. Cl.
    CPC ........ *A61B 17/0401* (2013.01); *A61B 17/683* (2013.01); *A61B 2017/0404* (2013.01); *A61B 2017/0409* (2013.01)
(58) Field of Classification Search
    CPC ........ A61B 17/0401; A61B 2017/0409; A61B 2017/0404; A61B 2017/0496; A61B 17/06166; A61B 17/683; A61B 2017/0046; A61B 17/0483

See application file for complete search history.

(56)      References Cited

U.S. PATENT DOCUMENTS

| | | | |
|---|---|---|---|
| 5,100,417 | A | 3/1992 | Cerier et al. |
| 6,716,234 | B2 | 4/2004 | Grafton et al. |
| 7,235,091 | B2 | 6/2007 | Thornes |
| 7,455,683 | B2 | 11/2008 | Geissler et al. |
| 7,951,178 | B2 | 5/2011 | Jensen |
| 8,348,960 | B2 | 1/2013 | Michel et al. |

(Continued)

FOREIGN PATENT DOCUMENTS

| | | |
|---|---|---|
| EP | 2085039 B1 | 3/2014 |
| EP | 4327755 A1 | 2/2024 |

(Continued)

OTHER PUBLICATIONS

Extended European Search Report issued in connection with European Patent Application No. 24177991.7, Oct. 11, 2024, 8 pages.

(Continued)

*Primary Examiner* — Katherine M Shi
(74) *Attorney, Agent, or Firm* — DUANE MORRIS LLP

(57)      ABSTRACT

A syndesmosis device inserter system includes a handle; a pusher assembly fit with the handle and including a body, a tube that is cannulated, and a rod fit into the tube; and a suture secured at a first end to a first half of the handle, threaded through a lateral button located in a groove of the handle and a medial button located at an end of the tube, and secured at a second end to a second half of the handle.

8 Claims, 42 Drawing Sheets

(56)  References Cited

U.S. PATENT DOCUMENTS

| | | | |
|---|---|---|---|
| 8,906,070 B2 | 12/2014 | Medoff | |
| 8,986,327 B2 | 3/2015 | Karasic et al. | |
| 9,056,003 B2 | 6/2015 | Demmer et al. | |
| 9,138,219 B2 | 9/2015 | Horrell et al. | |
| 9,179,950 B2 | 11/2015 | Zajac et al. | |
| 9,220,546 B2 | 12/2015 | Medoff et al. | |
| 9,277,912 B2 | 3/2016 | Donate et al. | |
| 9,839,455 B2 | 12/2017 | Cole | |
| 9,848,929 B2 | 12/2017 | Dacosta et al. | |
| 9,931,150 B2 | 4/2018 | Philippon et al. | |
| 9,943,304 B2 | 4/2018 | Branthover et al. | |
| 10,010,314 B2 | 7/2018 | Karasic et al. | |
| 10,010,316 B2 | 7/2018 | Karasic et al. | |
| 10,499,900 B2 | 12/2019 | Wade | |
| 10,617,408 B2 | 4/2020 | Karasic et al. | |
| 10,772,619 B2 | 9/2020 | Brunsvold et al. | |
| 11,013,506 B2 | 5/2021 | Moore | |
| 11,051,799 B2 | 7/2021 | Moore et al. | |
| 11,109,855 B2 | 9/2021 | Shoshtaev et al. | |
| 11,123,176 B2 | 9/2021 | Gordon | |
| 11,202,667 B2 | 12/2021 | Horrell et al. | |
| 11,229,456 B2 | 1/2022 | Awtrey et al. | |
| 11,234,688 B2 | 2/2022 | Taber et al. | |
| 12,161,319 B2 | 12/2024 | Earhart et al. | |
| 12,426,871 B2 * | 9/2025 | Evans | A61B 17/0483 |
| 2005/0240199 A1 | 10/2005 | Martinek et al. | |
| 2009/0043318 A1 | 2/2009 | Michel et al. | |
| 2012/0203249 A1 | 8/2012 | Schmidt et al. | |
| 2013/0053897 A1 | 2/2013 | Brown et al. | |
| 2013/0138108 A1 | 5/2013 | Dreyfuss et al. | |
| 2015/0039029 A1 | 2/2015 | Wade | |
| 2015/0051601 A1 | 2/2015 | Larsen et al. | |
| 2015/0250515 A1 | 9/2015 | Terrill et al. | |
| 2016/0262814 A1 | 9/2016 | Wainscott | |
| 2016/0354074 A1 | 12/2016 | Miller | |
| 2017/0027617 A1 | 2/2017 | Strnad | |
| 2017/0156767 A1 | 6/2017 | Chaudot et al. | |
| 2017/0252080 A1 | 9/2017 | Steinhauer et al. | |
| 2017/0258572 A1 | 9/2017 | Gordon | |
| 2018/0008330 A1 | 1/2018 | Taber et al. | |
| 2018/0049784 A1 | 2/2018 | Gault et al. | |
| 2018/0085110 A1 | 3/2018 | Earhart et al. | |
| 2018/0085112 A1 | 3/2018 | Sorensen et al. | |
| 2018/0153601 A1 | 6/2018 | Riley et al. | |
| 2018/0249998 A1 | 9/2018 | Chavan et al. | |
| 2018/0250045 A1 | 9/2018 | Austin et al. | |
| 2018/0271522 A1 | 9/2018 | Medoff | |
| 2020/0100781 A1 | 4/2020 | Brunsvold et al. | |
| 2021/0068809 A1 | 3/2021 | Federspiel et al. | |
| 2021/0121169 A1 | 4/2021 | Karasic et al. | |
| 2021/0177395 A1 | 6/2021 | Taylor et al. | |
| 2021/0290218 A1 | 9/2021 | Housman et al. | |
| 2021/0298740 A1 | 9/2021 | Taylor et al. | |
| 2021/0338227 A1 | 11/2021 | Federspiel et al. | |
| 2021/0378654 A1 | 12/2021 | Lombardo | |
| 2022/0079627 A1 | 3/2022 | Awtrey et al. | |
| 2022/0110623 A1 | 4/2022 | Karasic et al. | |
| 2022/0346768 A1 | 11/2022 | Pyle et al. | |
| 2024/0065686 A1 | 2/2024 | Evans et al. | |
| 2024/0065688 A1 | 2/2024 | Evans et al. | |
| 2024/0065689 A1 | 2/2024 | Evans et al. | |
| 2024/0423606 A1 | 12/2024 | Earhart et al. | |

FOREIGN PATENT DOCUMENTS

| | | |
|---|---|---|
| WO | 2018111275 A1 | 6/2018 |
| WO | 2021222698 A1 | 11/2021 |
| WO | 2022055962 A1 | 3/2022 |

OTHER PUBLICATIONS

File History of U.S. Appl. No. 17/821,982, filed Aug. 24, 2022, 368 pages.

File History of U.S. Appl. No. 15/278,804, filed Sep. 28, 2016, 586 pages.

File History of U.S. Appl. No. 18/180,941, filed Mar. 9, 2023, 181 pages.

* cited by examiner

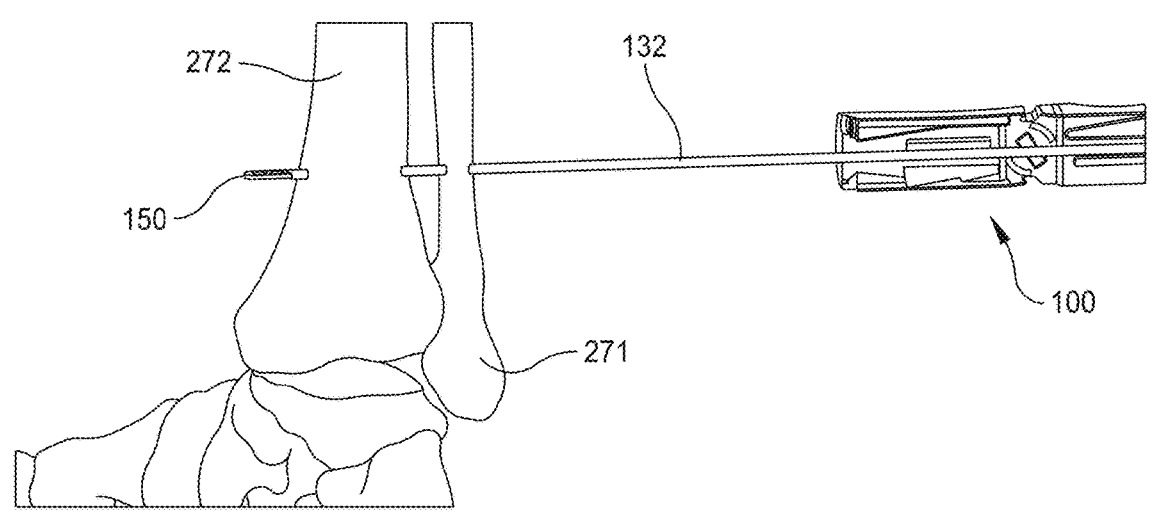
FIG. 27
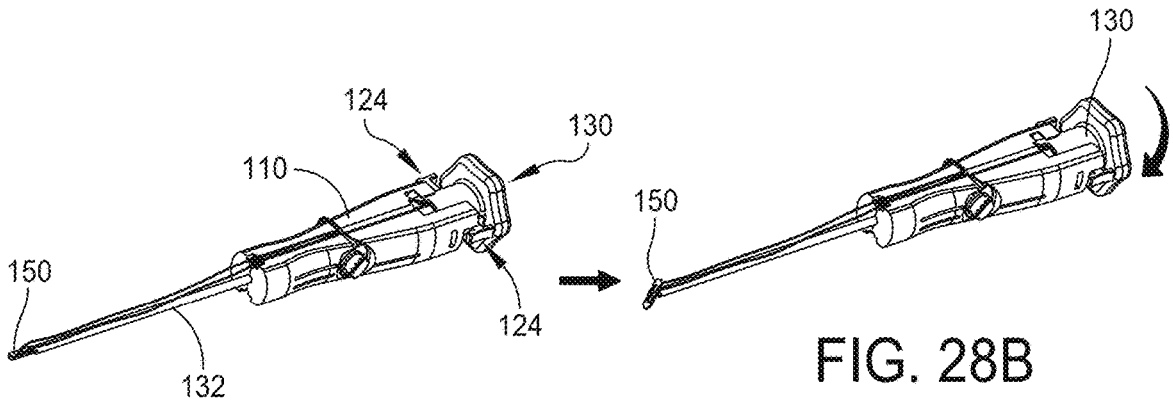
FIG. 28A
FIG. 28B
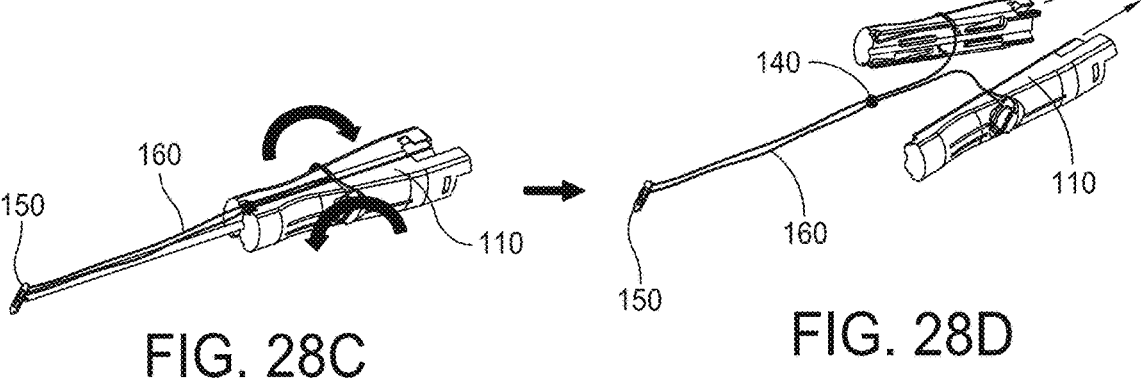
FIG. 28C
FIG. 28D

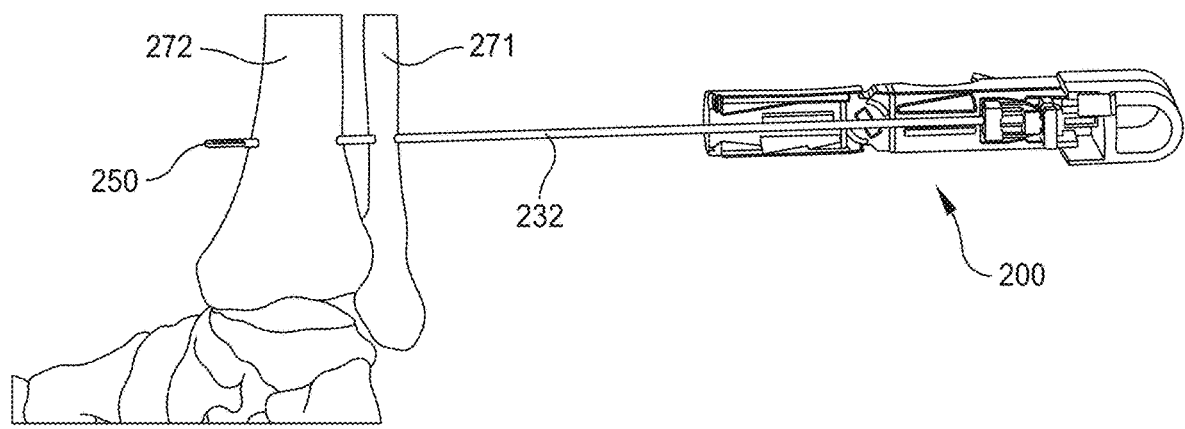
FIG. 47
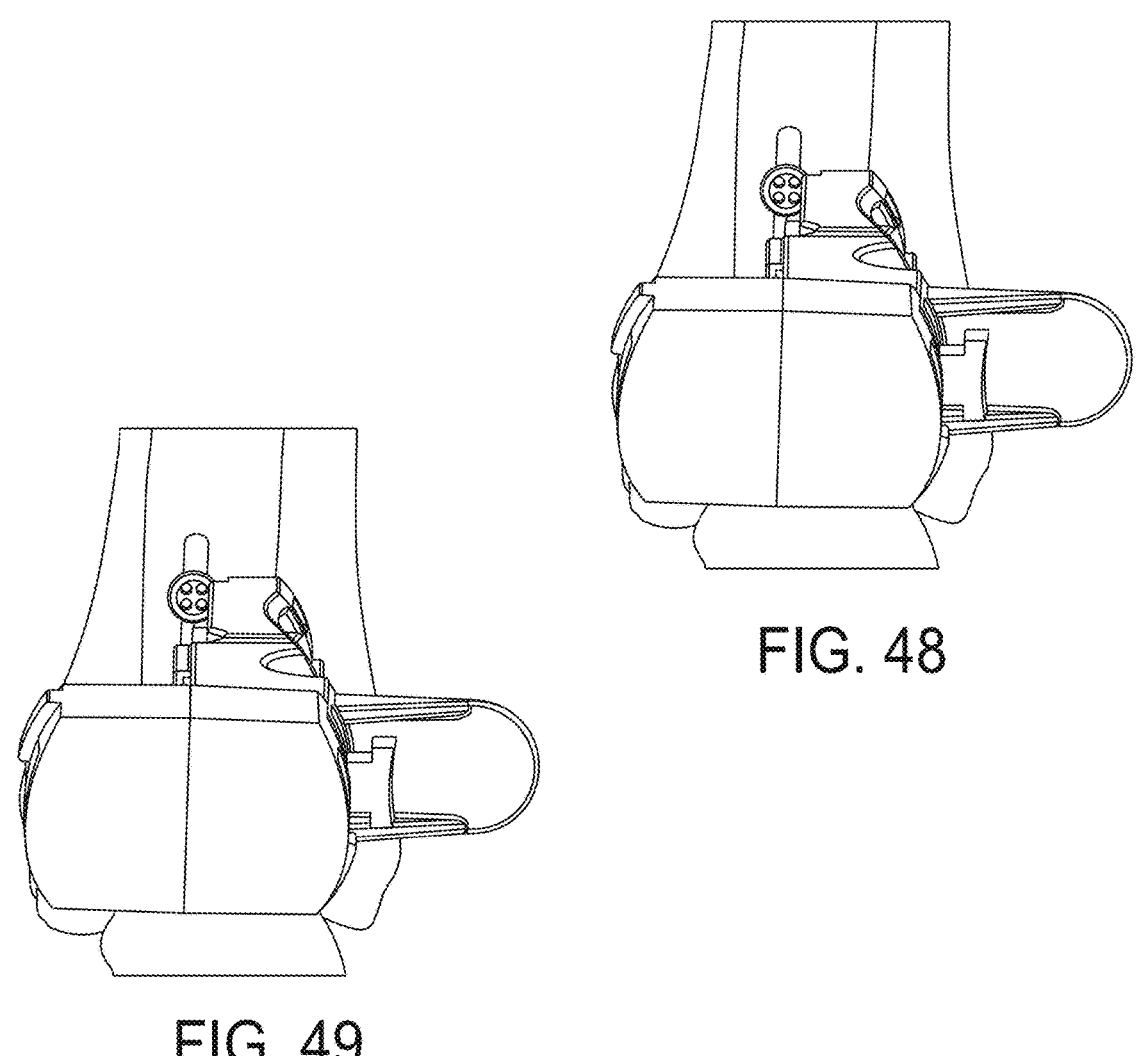
FIG. 48
FIG. 49

950

930

SYNDESMOSIS DEVICE INSERTER

CROSS REFERENCE TO RELATED APPLICATIONS

This application claims the benefit of U.S. Provisional Patent Application No. 63/504,470, filed May 26, 2023, the entire contents of each of which is incorporated by reference for all purposes as if fully set forth herein.

BACKGROUND

Various bodily injuries include separation of soft tissue from one or more bones and/or separation of bones from normally anatomical correct positioning. Maintaining the bones in the correct anatomical positions during healing is important to provide proper soft tissue reattachment and proper bone healing. For example, during syndesmosis repair, a first bone and a second bone must be maintained in a fixed position to allow the connective tissue to refuse.

A suture-button construct can be passed through a passage or a hole drilled through a bone by a needle that pulls the button and the attached suture through the hole. A button inserter can be used to pass the button attached to a suture through the hole for positioning of the button on the cortex of a bone. Pull-through sutures and a needle advance a suture button through a bone tunnel and position the button onto the distal cortical surface of the bone. The use of pull-through sutures and needle associated with an "inside-out" technique can cause a surgeon to advance the suture button farther than necessary to deploy and flip the button into its position on the bone cortex. Proper positioning of the buttons can be difficult when the buttons are pulled through with suture and needle. In addition, advancing the button farther than necessary can also cause soft-tissue to become trapped underneath the button when seated on the bone cortex resulting in the button being positioned proud of the bone surface.

An instrument to push the buttons and attached suture through the drilled hole (instead of having to pull them through using the needle) is needed. Methods of advancing suture-button constructs through drilled tunnels or holes, particularly in situations where the needle and attached suture/button construct cannot be easily pulled through the hole and out the skin, are also needed.

SUMMARY OF THE DISCLOSURE

To overcome the problems described above, embodiments of the present disclosure include syndesmosis device inserters and a button-suture construct that can be pushed through drilled holes.

The syndesmosis device inserter allows for the implantation of a syndesmosis device without a medial incision. It also permits tensioning without having to attach other instruments or tension by hand.

According to an embodiment, a syndesmosis device inserter system includes a handle; a pusher assembly fit with the handle and including a body, a tube that is cannulated, and a rod fit into the tube; and a suture secured at a first end to a first half of the handle, threaded through a lateral button located in a groove of the handle and a medial button located at an end of the tube, and secured at a second end to a second half of the handle.

The system can further include a locking button to lock and unlock the pusher assembly from the handle.

In an aspect, the handle is configured such that the first half and the second half are rotatable relative to each other to separate the two halves and release the lateral button from the handle.

In an aspect, the body includes an extending portion that includes two release tabs and a claw configured to couple to a retainer attached to the rod.

In an aspect, in a locked state, the locking button prevents the pusher assembly from moving with respect to the handle, and in an unlocked state, the locking button permits the pusher assembly to move with respect to the handle.

In an aspect, in an unlocked state, the body is configured to move with respect to the handle to force the rod down the tube and release the medial button from the tube.

In an aspect, the first half and the second half are identical.

In an aspect, the medial button is oblong and secured into a notch of the tube in an axial alignment.

In an aspect, the first half and the second half are configured to provide tension to pull the first end and the second end.

In another embodiment, a surgical device includes a suture construct including a suture secured at a first end to a first half of a handle, fed through a lateral button on the handle and a medial button at an end of a rod protruding from the handle, and secured at a second end to a second half of the handle, wherein the first half and the second half are configured to be separated and provide tension to the suture to force the lateral button and the medial button together.

The surgical device can further include a pushing device attached to the handle and the rod and configured to push the medial button away from the rod.

In an aspect, the pushing device is configured to be separated from the handle.

In an aspect, the pushing device is configured to push the medial button away from the rod after being unlocked from the handle and configured to separate the rod from the handle after being rotated to a hard stop position.

In an aspect, the pushing device includes a lock that must be unlocked to push the medial button away from the rod.

In another embodiment, a surgical method includes defining a tunnel through a first bone and a second bone; inserting a portion of a bone anchor device including a rod, a medial button at a first end of the rod, and a portion of a suture fed through the medial button through the tunnel; forcing the rod in a first direction to deploy the medial button from the bone anchor device to be against an outer surface of the second bone; removing the rod from the tunnel in a second direction; and tensioning the suture to force the first bone and the second bone together.

In an aspect, the rod is forced in the first direction via a pusher that has been unlocked from a handle of the bone anchor device.

The method can further include unlocking the pusher by pressing a locking button to a first unlock position.

In an aspect, the forcing the rod in the first direction to deploy the medial button includes pushing the medial button from a notch in a tube around the rod.

The method can further include unlocking a pusher from a handle of the bone anchor device before using the pusher for forcing the rod in the first direction.

The method can further include unlocking a pusher within a handle of the bone anchor device, and pushing the pusher to secure the rod before removing the rod from the tunnel by pulling the pusher.

In an aspect, unlocking the pusher includes pressing a locking button to a second unlock position.

In an aspect, the tensioning the suture includes pulling on a first end of the suture via a first half of a handle of the bone anchor device and pulling on a second end of the suture via a second half of the handle, and the first end and the second end are attached to the first half and the second half, respectively, before inserting the portion of a bone anchor device through the tunnel.

The method can be performed in a syndesmosis surgery.

The above and other features, elements, characteristics, steps, and advantages of the present invention will become more apparent from the following detailed description of preferred embodiments of the present invention with reference to the attached drawings.

BRIEF DESCRIPTION OF THE DRAWINGS

FIG. 27 to FIG. 28D show how the syndesmosis device inserter can be used during ankle surgery.

FIG. 47 to FIG. 59 show how a syndesmosis device inserter can be used during a surgical technique, for example during ankle surgery.

DETAILED DESCRIPTION

Figure 1:
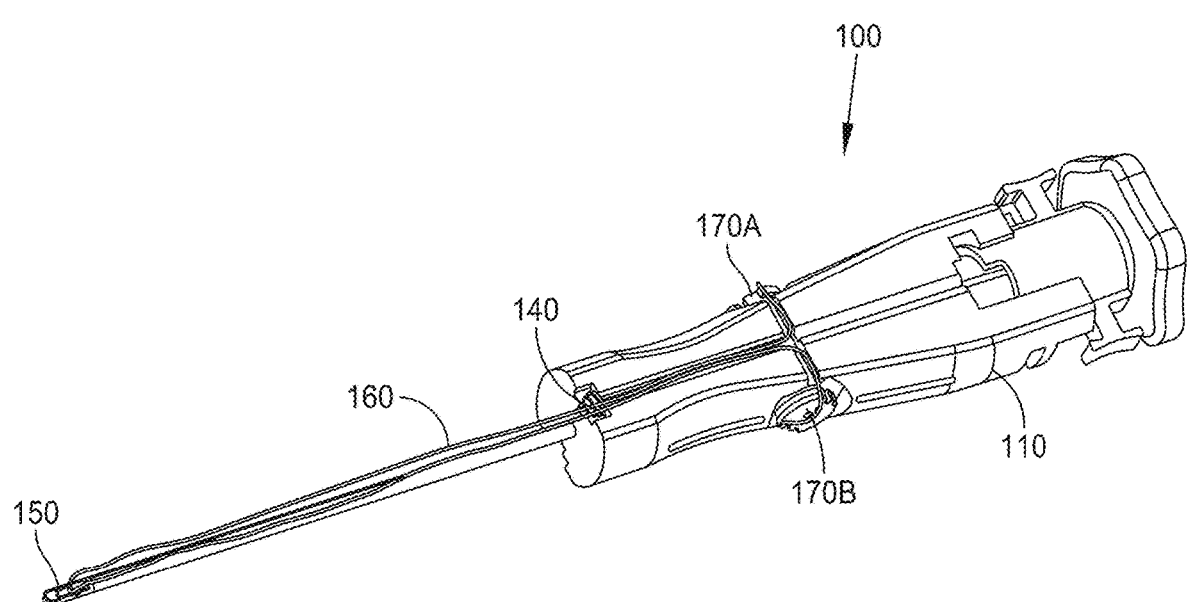
FIG. 1 is a perspective view of a syndesmosis device inserter according to one embodiment of the present disclosure.

In the following description, reference is made to the accompanying drawings that form a part thereof, and in which is shown by way of illustrating specific exemplary embodiments in which the disclosure may be practiced. These embodiments are described in sufficient detail to enable those skilled in the art to practice the concepts disclosed herein, and it is to be understood that modifications to the various disclosed embodiments may be made, and other embodiments may be utilized, without departing from the scope of the present disclosure. The following detailed description is, therefore, not to be taken in a limiting sense.

Reference will now be made in detail to embodiments of the present disclosure, examples of which are illustrated in the accompanying drawings. Whenever possible, the same reference numerals will be used throughout the drawings to refer to the same or like parts. However, this disclosure may be embodied in many different forms and should not be construed as limited to the embodiments set forth herein.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected," refer to a relationship wherein structures are secured or attached to one another either directly or indirectly through intervening structures, as well as both movable or rigid attachments or relationships, unless expressly described otherwise.

Unless otherwise expressly stated, it is in no way intended that any method set forth herein be construed as requiring that its steps be performed in a specific order, nor that with any apparatus, specific orientations be required. Accordingly, where a method claim does not actually recite an order to be followed by its steps, or that any apparatus claim does not actually recite an order or orientation to individual components, or it is not otherwise specifically stated in the claims or description that the steps are to be limited to a specific order, or that a specific order or orientation to components of an apparatus is not recited, it is in no way intended that an order or orientation be inferred, in any respect. This holds for any possible non-express basis for interpretation, including: matters of logic with respect to arrangement of steps, operational flow, order of components, or orientation of components; plain meaning derived from grammatical organization or punctuation, and; the number or type of embodiments described in the specification.

As used herein, the singular forms "a," "an," and "the" include plural references unless the context clearly dictates otherwise. Thus, for example, reference to "a" component includes aspects having two or more such components, unless the context clearly indicates otherwise.

Figure 2:
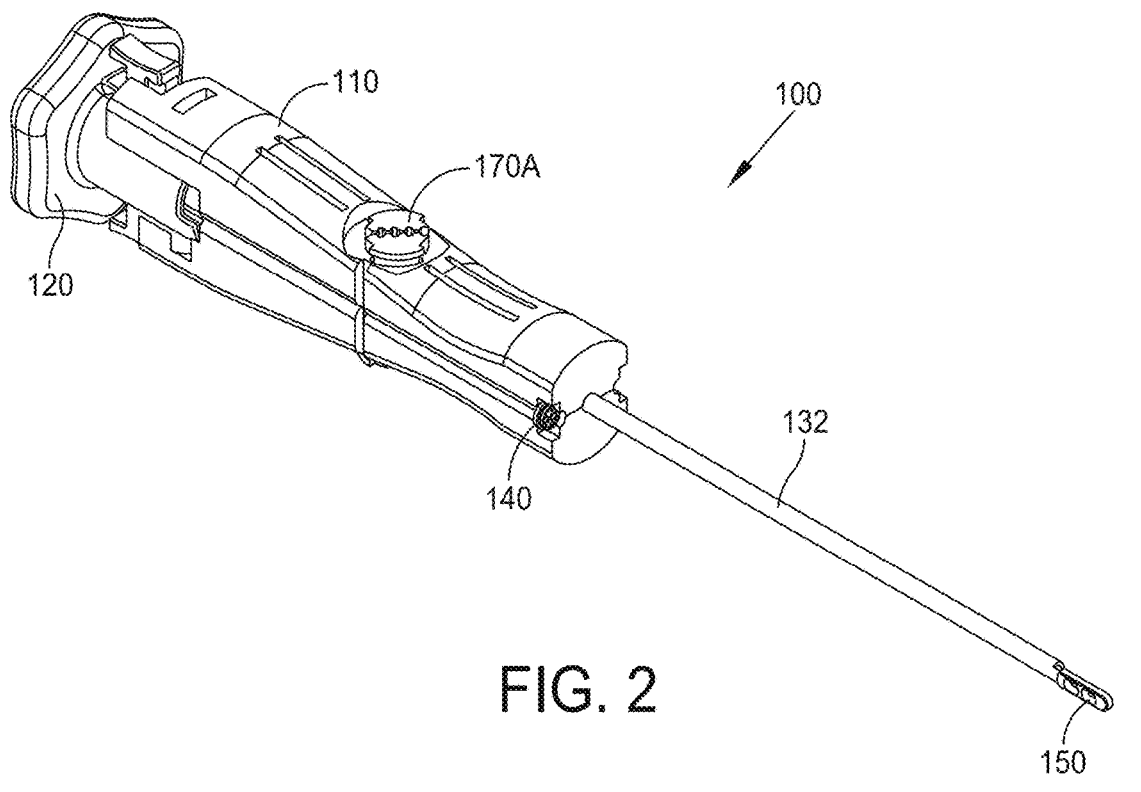
FIG. 2 is an exploded view of the syndesmosis device inserter of FIG. 1.
Figure 3:
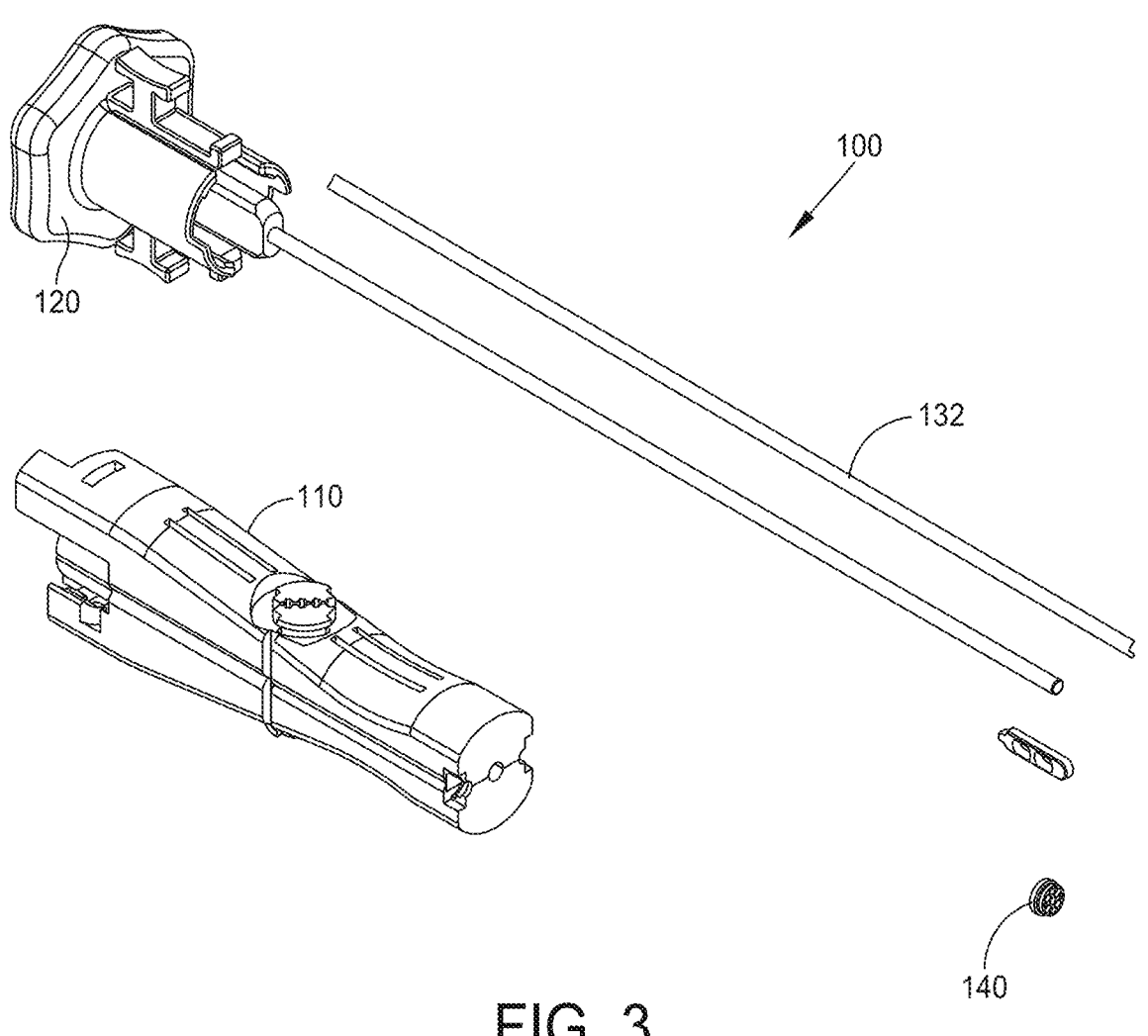
FIG. 3 is a perspective view of a syndesmosis device inserter.

FIGS. 1 and 2 are perspective views and FIG. 3 is an exploded view of a syndesmosis device inserter 100 according to an embodiment of the current disclosure. As shown, the syndesmosis device inserter 100 can include a handle 110, a knob 120 assembly, a tube 132, a lateral button 140, a medial button 150, and a suture 160.

FIG. 1 shows that the suture 160 can be threaded through both the lateral button 140 and the medial button 150 with each end of the suture 160 wound around a corresponding suture cleat or post 170A and 170B that are located on the handle 110.

Figure 4:
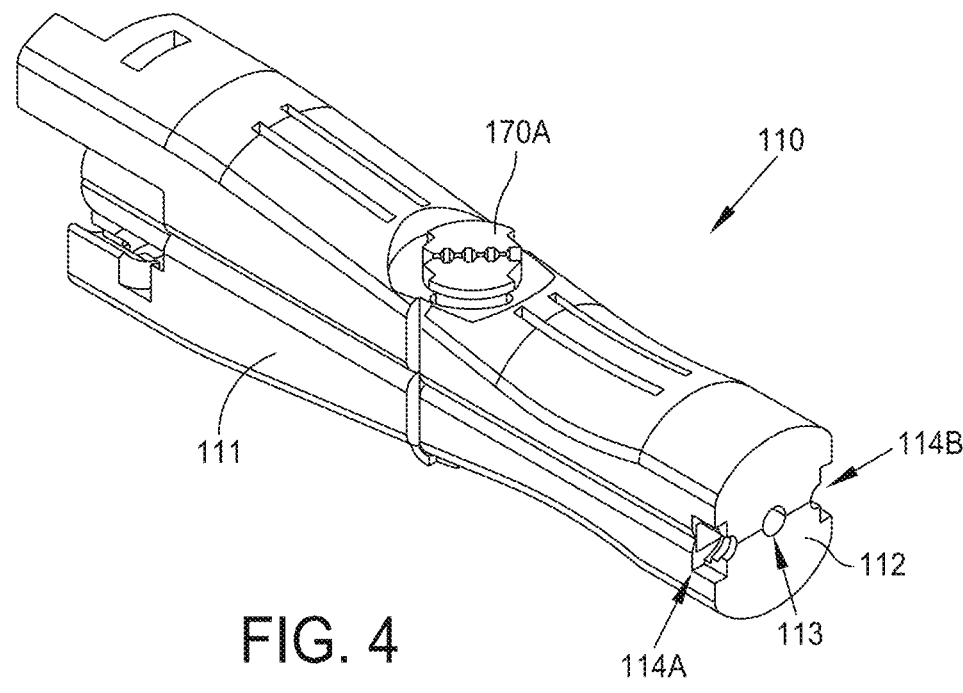
FIG. 4 and FIG. 5 are perspective views of a handle.
Figure 5:
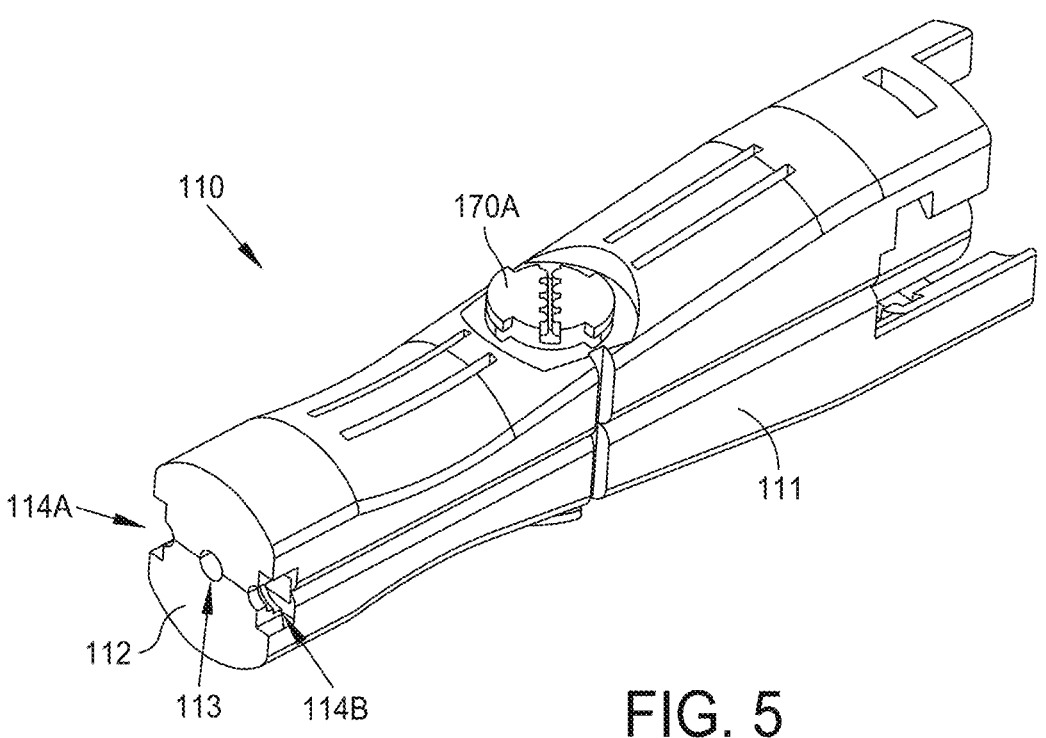

FIGS. 4 and 5 are perspective views of the handle 110. As shown, the handle 110 can include two identical halves that when joined together define a body 111 that can be generally cylindrical such that a user can grip the handle 110 and a syndesmosis device inserter 100 in which the handle 110 is a part. At a distal end 112, the handle 110 can include an opening 113 from which the knob assembly 120 can extend through, as seen in FIGS. 1 and 3. The distal end 112 can also include at least one groove 114A and 114B in which a lateral button 140 can be located. In an aspect, the distal end 112 can include two opposing grooves 114A and 114B. The grooves 114A, 114B can be sized and configured to accept a lateral button 140.

Figure 6:
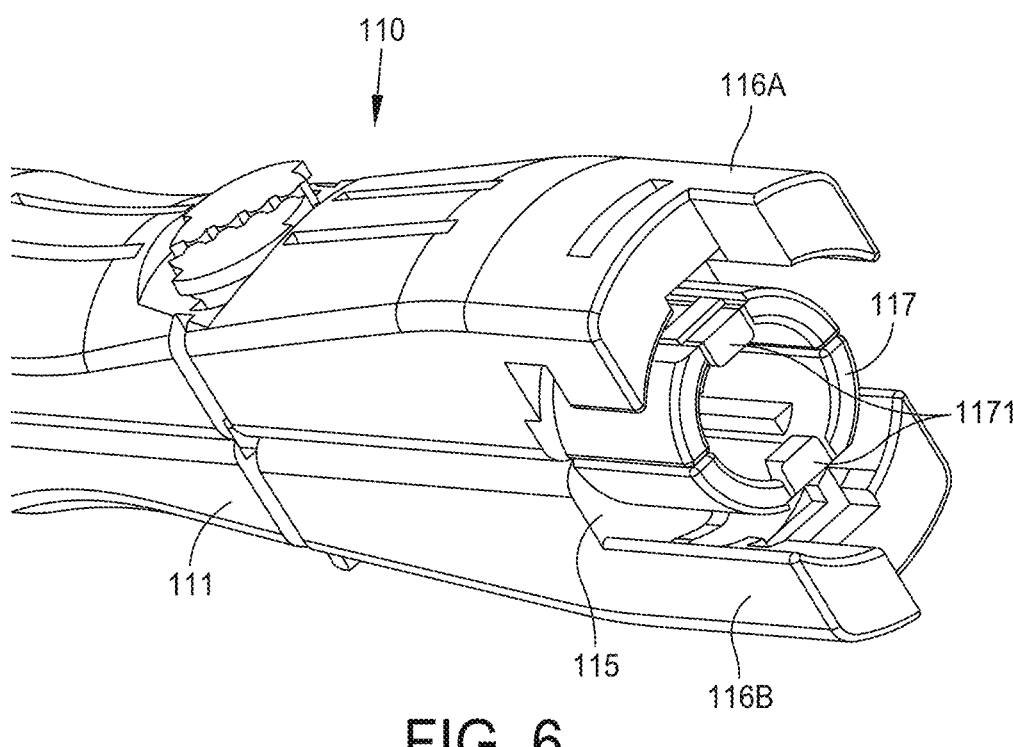
FIG. 6 is a perspective view of a proximal end of the handle.

FIG. 6 is a perspective view of a proximal end 115 of the handle 110. The proximal end 115 can include features used to retain the knob assembly 120 and the tube 132. These features can include cutout flanges 116A and 116B that extend about a more central tubular portion 117. Additionally, the central tubular portion 117 can include retaining tabs 1171 that secure the retainer 134 and the rod 136 of the knob assembly 120.

Figure 7:
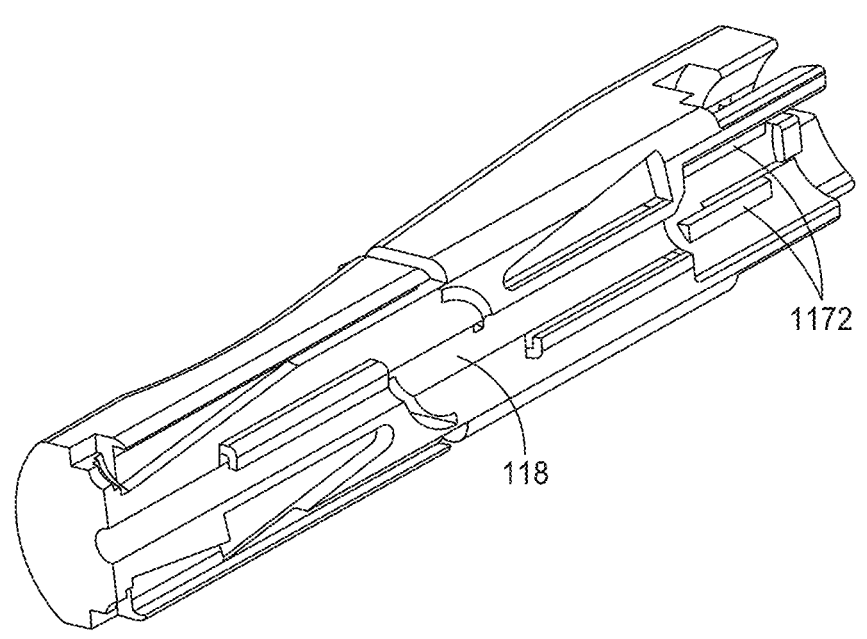
FIG. 7 is a perspective view of an inner portion of one half of the handle.

FIG. 7 is a perspective view of an inner portion of one half of the handle 110. As shown, the inner portion can include a cylindrical bore 118 defined through the center in which the rod 136 and tube 132 can be located. There are additional features of the inner portion that connects the handle 110 to the knob assembly 120 and the tube 132. Mentioned above are the retaining tabs 1171. There are also two rails 1172 in both of the two halves of the handle 110 that maintain the orientation of the knob assembly 120.

Figure 8:
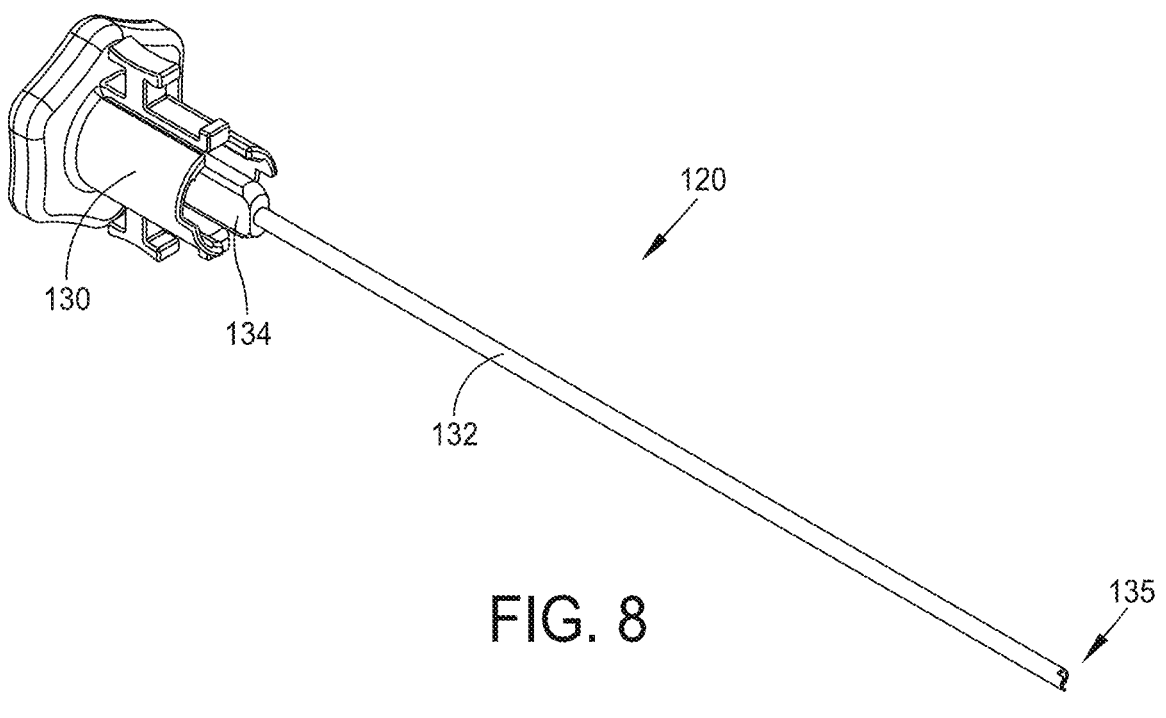
FIG. 8 and FIG. 9 are perspective views of a tube assembly.
Figure 9:
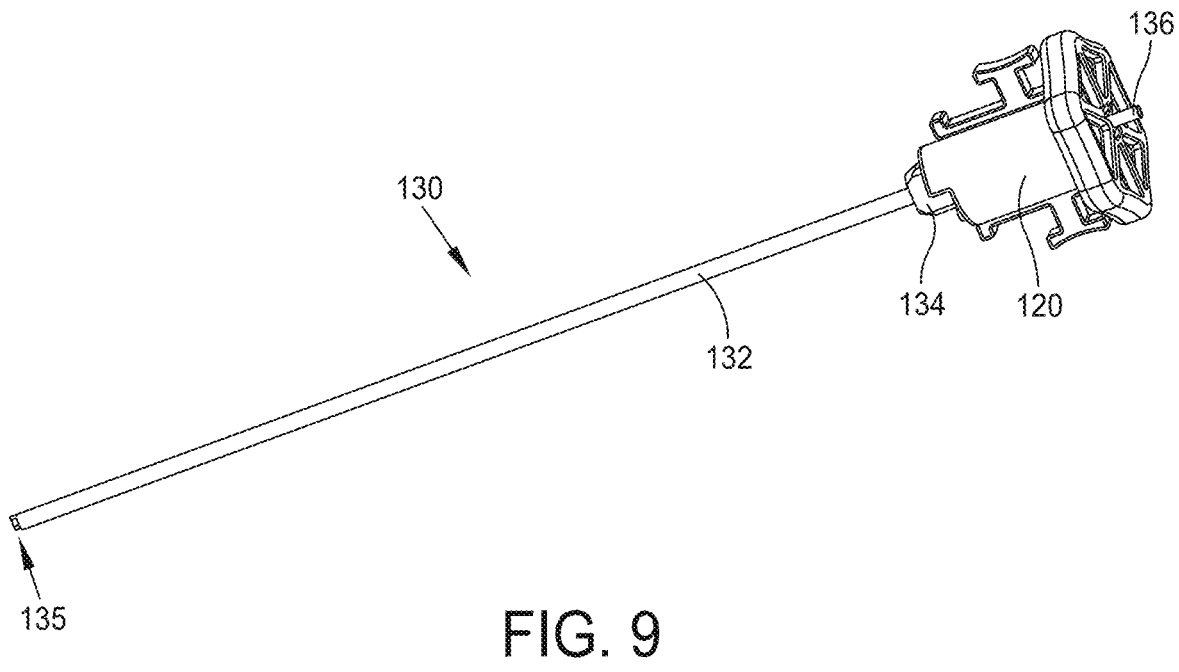

FIGS. 8 and 9 are perspective views of the knob assembly 120. As shown, the knob assembly 120 can include a cannulated tube 132 that includes a cutout portion defining a notch 135 at one end of the tube 132, a retainer 134, a rod 136, and a knob 130. The knob 130 can be integrally molded with and attached to the rod 136. The notch 135 can be used to retain the medial button 150 that can be press fit into the notch 135. The retainer 134 can be force fit over an end of the rod 136 opposite from the notch 135 or overmolded with the knob 130 and the rod 136. The retainer 134 can include geometric features used to mate with and be secured by features of inner portions of the handle 110. The rod 136 fits into a lumen or bore of the tube 132 and extends from an end of the tube 132 and is moveable with respect to the tube 132. The rod 136 is free to move within the tube 132 and is attached to the knob 130, which when pushed moves the rod 136 through the tube 132.

Figure 10:
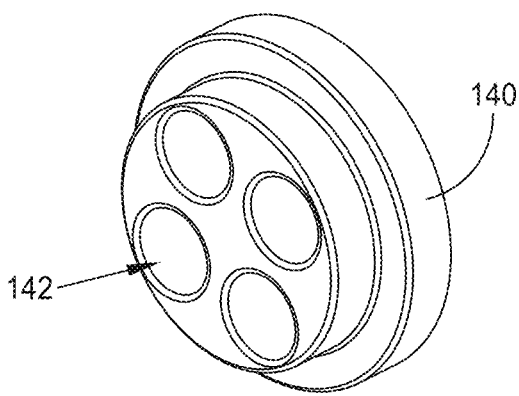
FIG. 10 is a perspective view of a lateral button.

FIG. 10 is a perspective view of the lateral button 140. The lateral button 140 can be round or rounded with one portion having a greater diameter than another portion and include two opposing flat surfaces. The lateral button 140 can be sized and configured to fit into a groove 114A, 114B of the handle 110. The lateral button 140 can include at least one through hole 142 in which the suture 160 can be thread through.

Figure 11:
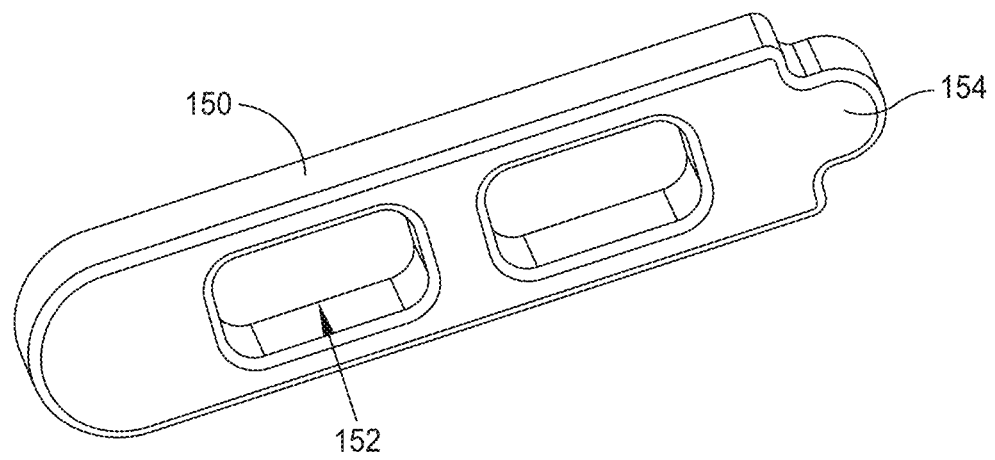
FIG. 11 is a perspective view of a medial button.

FIG. 11 is a perspective view of the medial button 150. The medial button 150 can be oval or oblong and include one rounded end, one end including a protrusion 154 that is narrower than a width of a minor axis of the medial button 150, and two opposing flat surfaces. The medial button 150 can be sized and configured to fit the protrusion 154 into the notch 135 of the tube 132. The medial button 150 can include at least one through hole 152 in which the suture 160 can be thread through. The protrusion 154 can be rectangular or square in cross section with rounded edges to ease insertion into the notch 135 of the tube 132. In an alternative embodiment, not shown, the protrusion 154 can be more circular in cross-section to fit within the circular tube 132. The wall thickness of the tube 132 is designed to retain the protrusion 154 and medial button 150 in an axial alignment, wherein under extreme load the tube 132 would crack before the protrusion 154 could snap off and either fail or leave a fragment in a patient.

The lateral button 140 and the medial button 150 can be made of a material including a metal such as stainless steel, titanium alloy, titanium, a plastic such as polyetheretherketone (PEEK) or Polylactide (PLLA), or any other suitable material.

Figure 12:
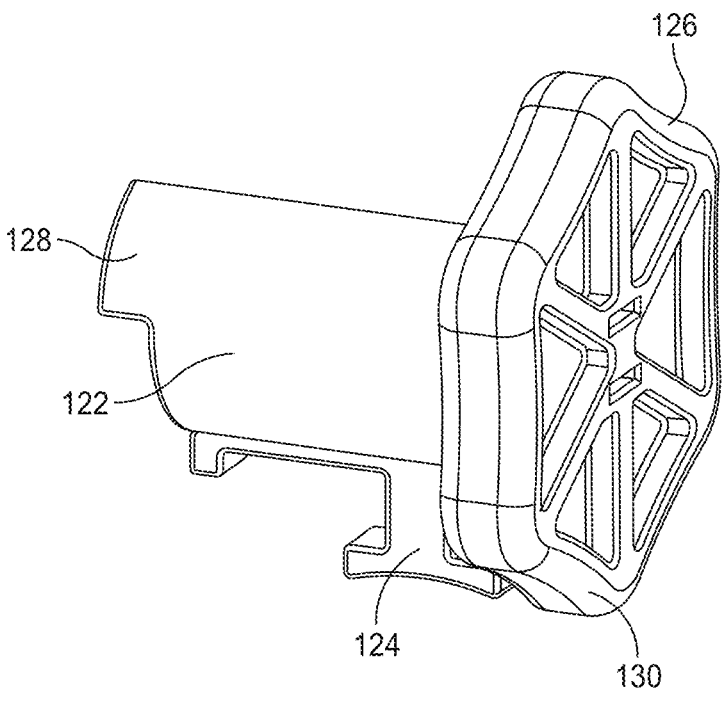
FIG. 12 and FIG. 13 are perspective views of a knob.
Figure 13:
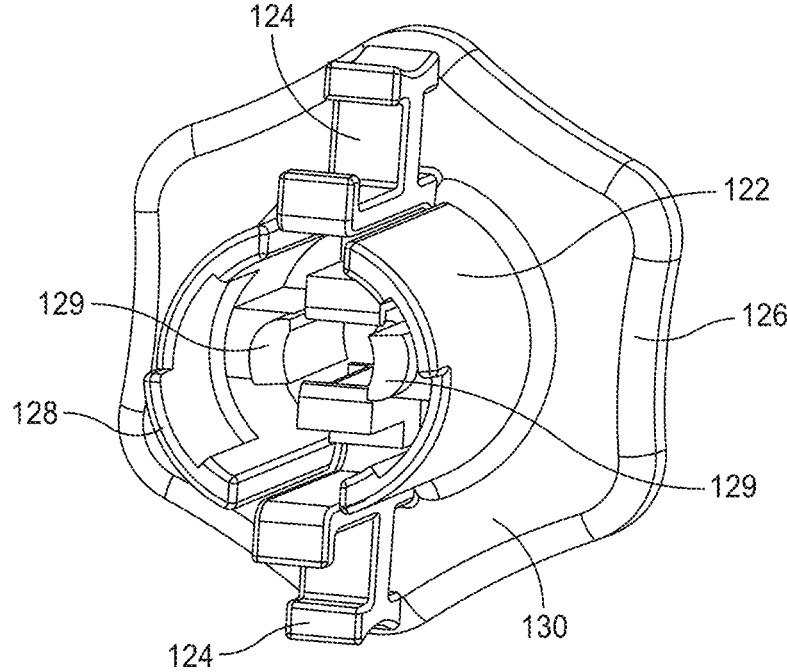

FIGS. 12 and 13 are perspective views of the knob 130. The knob 130 can include a body 122, two opposing push buttons 124, and a grip 126. The body 122 can be generally rounded and configured to fit over the central tubular portion 117 of the handle 110. Portions of the body 122 can include keying features 128 that can be configured to fit with the cutout flanges 116A and 116B. The push buttons 124 can project from the grip 126 and can include a surface 125 for pressing and a tab 127. The push buttons 124 can be projected from the grip 126 such that pressing the surface 125 or both surfaces 125 toward each other provides a force that moves the tabs 127 toward a center of the body 122. The grip 126 can be generally circular, hexagonal, rectangular, or any suitable shape that the grip 126 can be grabbed by a surgeon to rotate the knob 130. When the knob 130 is rotated, the push tabs 129 line up with the retainer 134 and when the knob 130 is pushed, the push tabs 129 release the retainer 134 from the handle 110.

Figure 14:
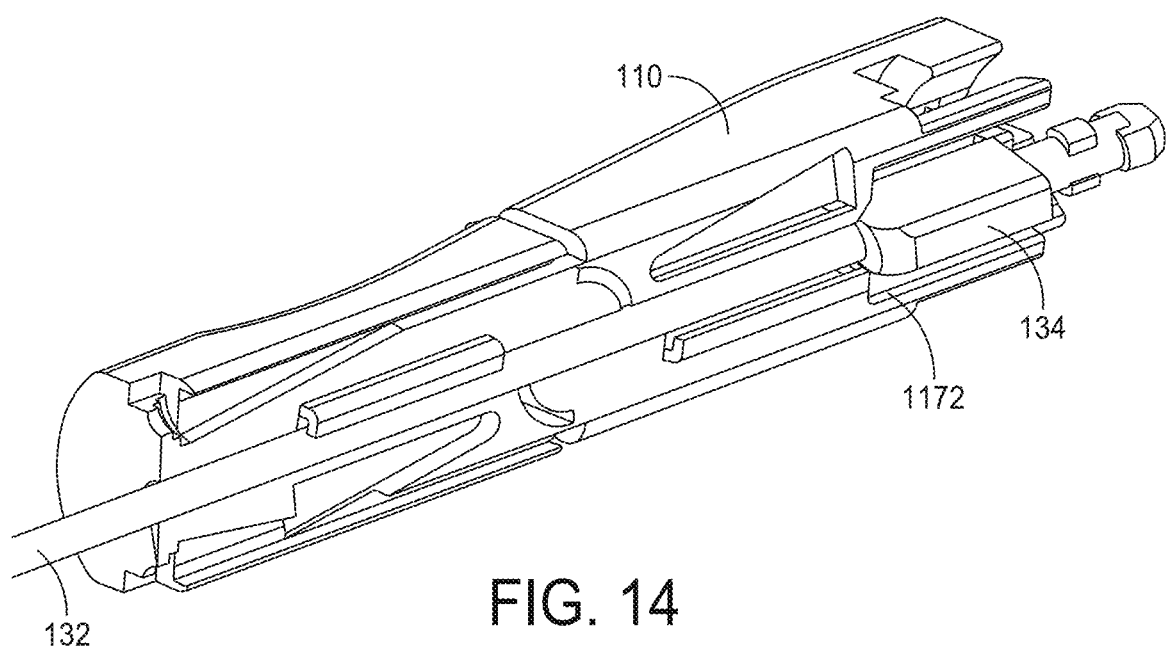
FIG. 14 and FIG. 15 show a subassembly including the tube assembly fit into the handle.
Figure 15:
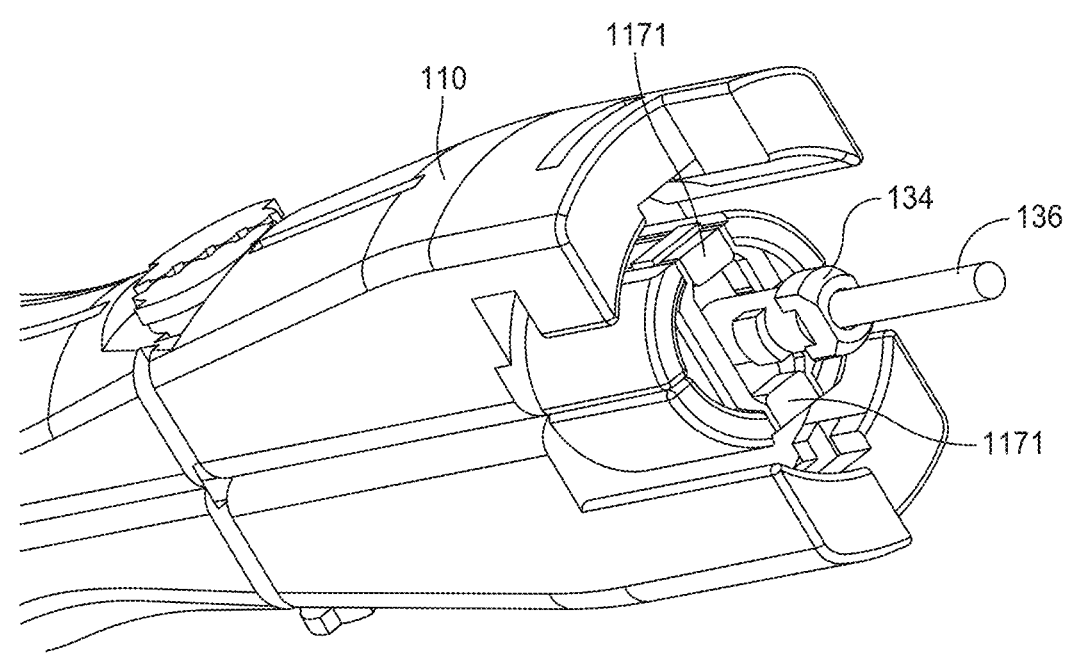

FIGS. 14 and 15 show a subassembly including the knob assembly 120 fit into the handle 110 (the knob 130 is omitted for clarity). FIG. 14 is a cutaway view that shows one half of the handle 110 with the retainer 134 force fit and held in place by rails 1172. The Tube 132 is aligned with and oriented in the bore 118 of the handle 110. FIG. 15 is a perspective view showing the knob assembly 120 positioned within the handle 110 with the knob 130 removed to show an end of the retainer 134 and the rod 136 protruding from the proximal end of the handle 110. This arrangement ensures that the knob assembly 120 is secured within the handle 110 and retained so that the rod 136 can be moved in and out with respect to the handle 110.

Figure 16:
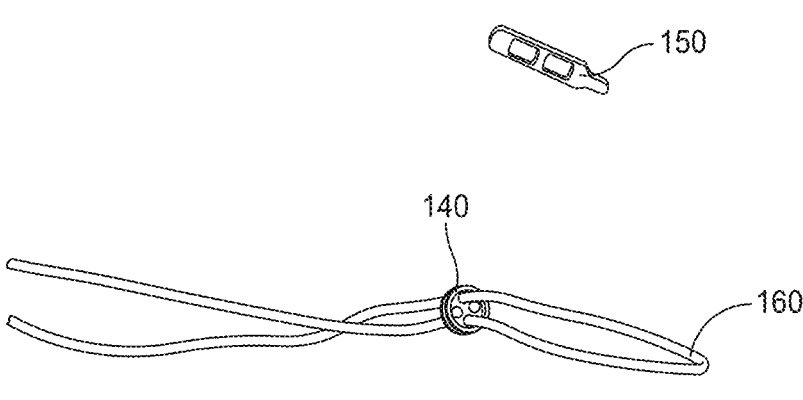
FIG. 16 to FIG. 23 show an example how a suture and buttons can be assembled.
Figure 17:
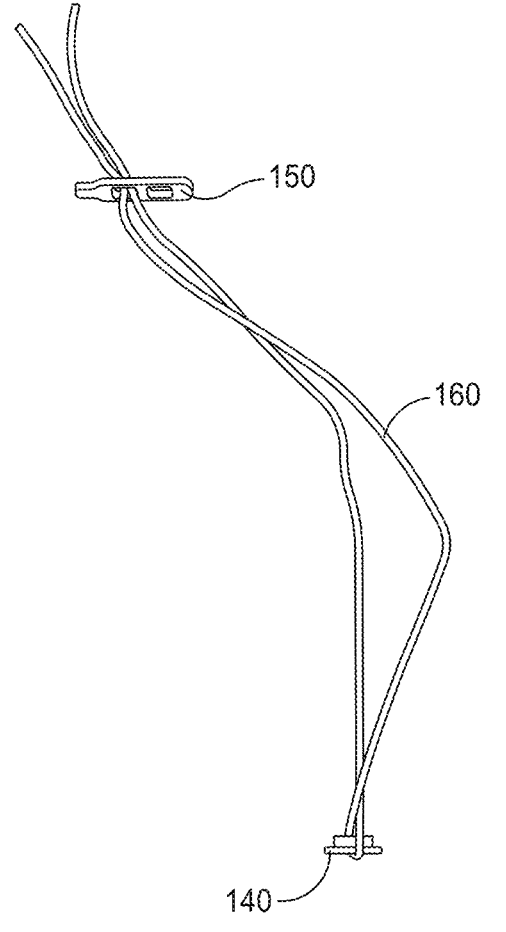
Figure 18:
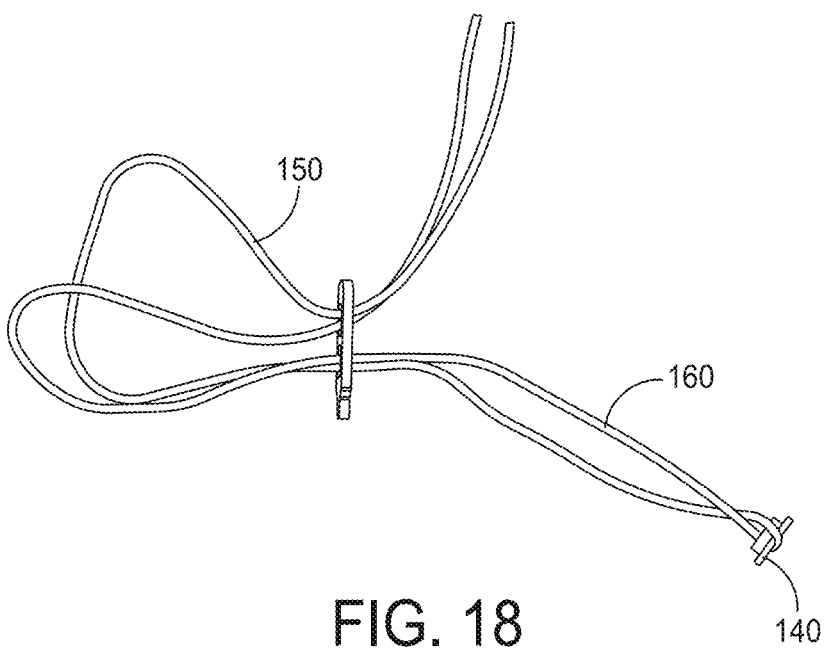
Figure 19:
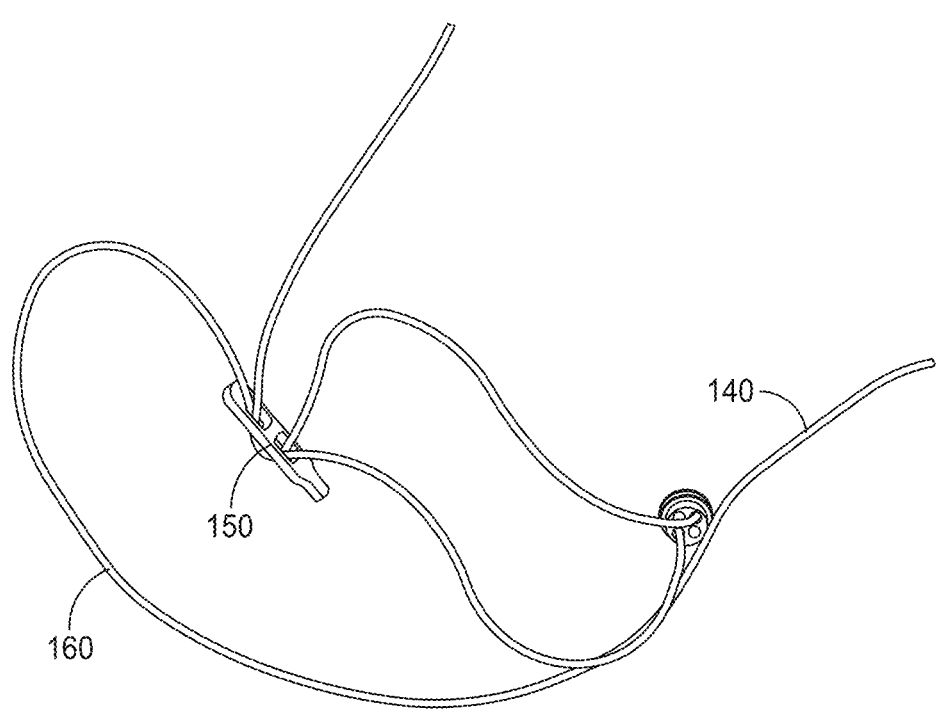
Figure 20:
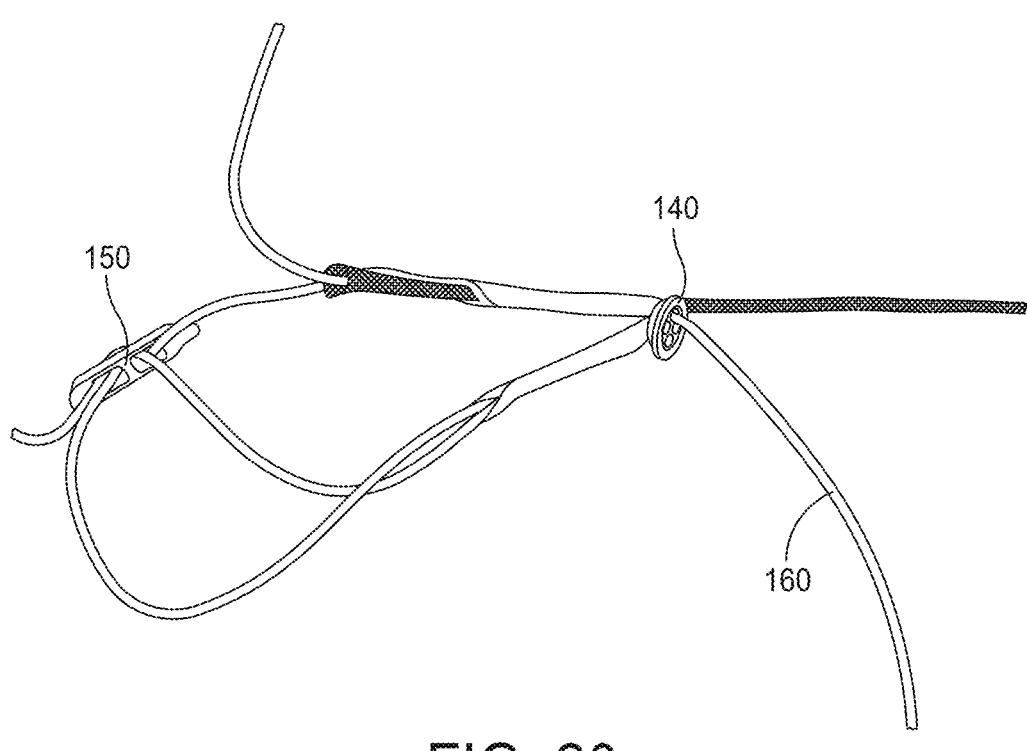
Figure 21:
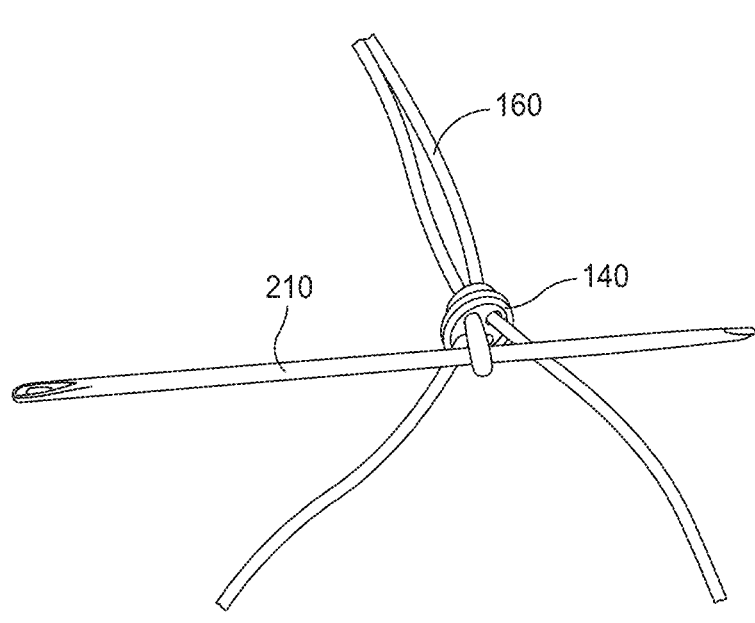
Figure 22:
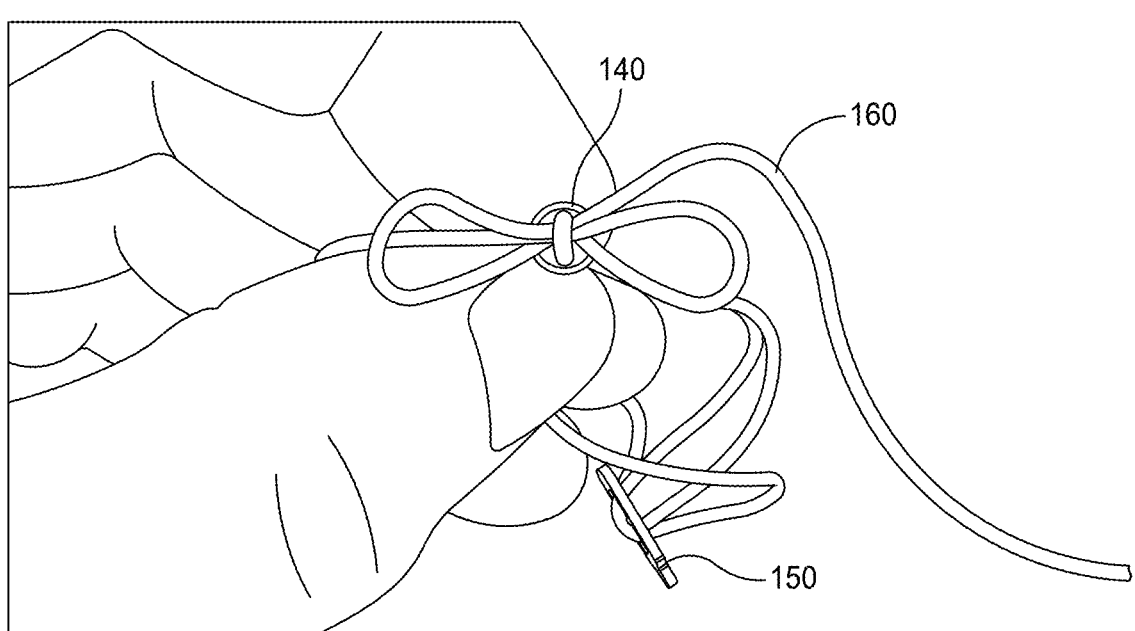
Figure 23:
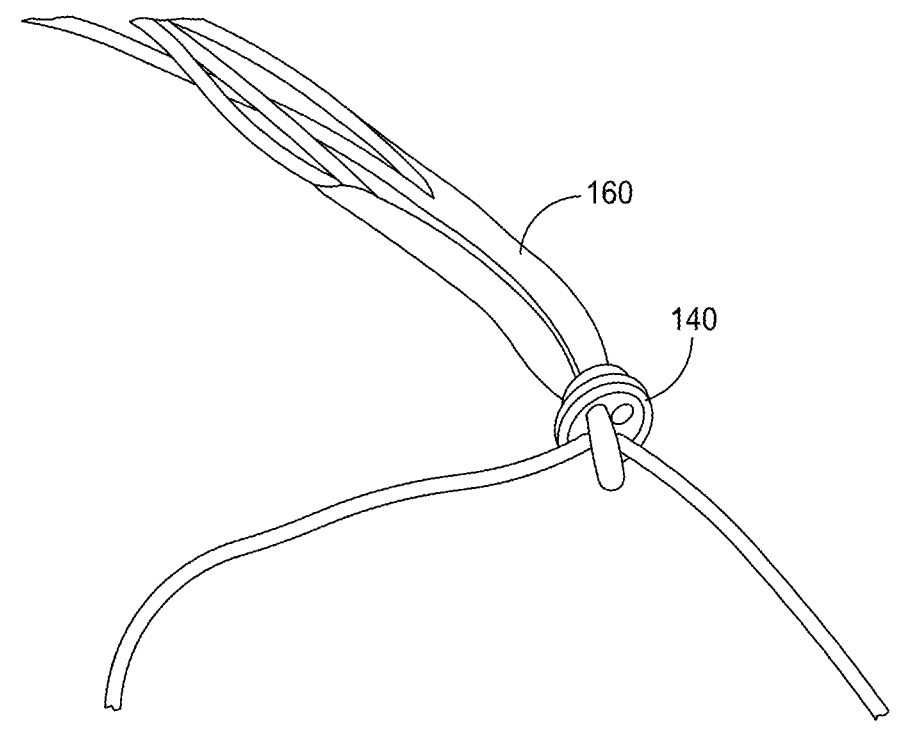

FIGS. 16 to 23 show an example how a suture and buttons can be assembled. FIG. 16 shows that two ends of the suture 160 can be passed through two opposing holes in the lateral button 140. FIGS. 17 and 18 show that two strands of the suture 160 can be passed through one hole of the medial button 150 (FIG. 17) and then back through the other hole in the medial button 150 (FIG. 18). FIG. 19 shows that the individual strands of the suture 160 can be then threaded back through their respective strands. FIG. 20 shows that once the strands are passed through tunnels of the suture 160 they are passed through the remaining two holes of the lateral button 140. FIG. 22 shows that the two strands can then be passed under a main loop of the suture 160 where a needle 210 has been is placed, as shown in FIG. 21. Once the two strands are passed under the main loop of the suture 160, they are pulled completely through to remove the "bow" looking arrangement shown in FIG. 22. Once those bow loops are pulled through the arrangement looks like that shown in FIG. 23.

Figure 24:
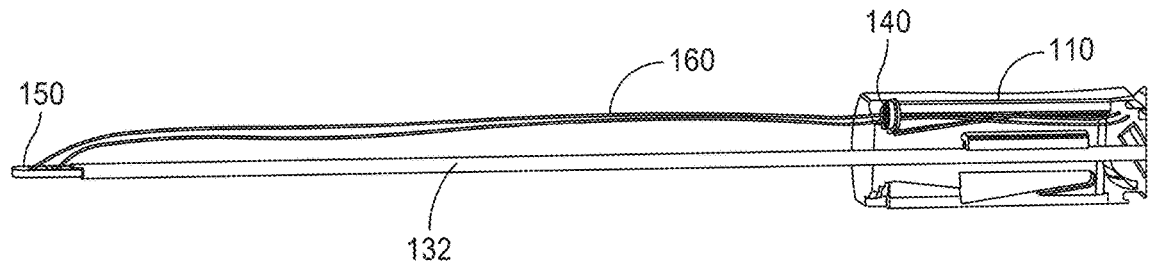
FIG. 24 to FIG. 26 show how the buttons and the suture can be assembled onto a handle/tube assembly.
Figure 25:
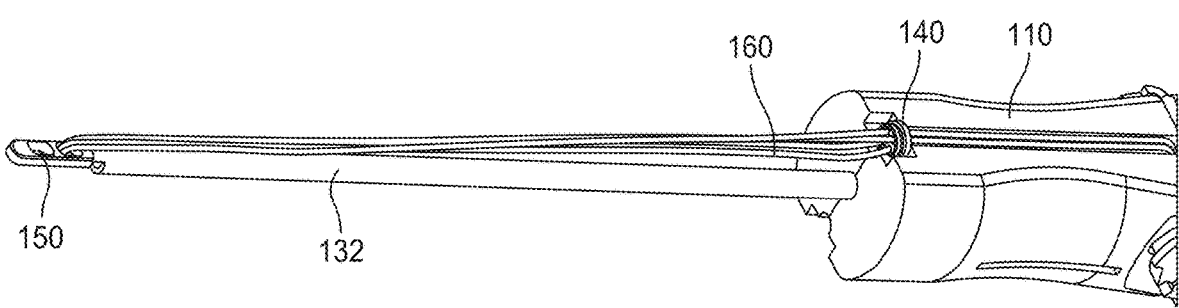
Figure 26:
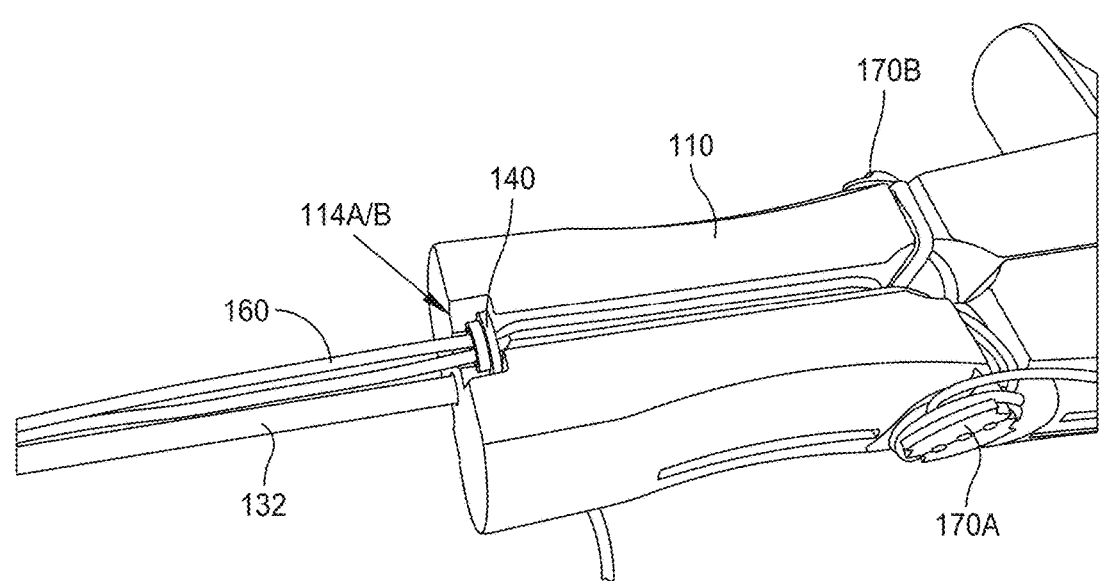

FIGS. 24 to 26 show how the buttons 140, 150 and the suture 160 can be assembled onto a handle 110/knob assembly 120. As shown in FIGS. 24 and 25, the medial button 150 can be press fit into the notch 135 at the end of the tube 132 and the lateral button 140 can be press fit into one of the grooves 114A, 114B. The suture 160 can be routed through the lateral button 140, the medial button 150, and a longitudinal groove define in the housing 110, as shown in FIGS. 25 and 26. FIG. 26 also shows that strands of the suture 160 can be wrapped around or knotted to the suture posts 170A, 170B. In this state, the syndesmosis device inserter 100 is ready for use by the surgeon.

FIGS. 27 to 28D show how the syndesmosis device inserter 100 can be used during a surgical technique, for example during ankle surgery. After an incision is made on the lateral side of the ankle, a hole is drilled from the lateral side of the fibula 271 through the tibia 272. FIG. 27 shows that the medial button 150 and suture construct is inserted, through the hole made in the fibula 271 and then through both cortices of the tibia 272 until the tube 132 is flush to the medial cortex of the tibia 272.

FIG. 28A shows that once the medial button 150 is in beyond the medial cortex of the tibia 272 and fully exited the tibia 272, the two push buttons 124 of the knob 130 are depressed to release the knob 130 from the handle 110 and the knob 130 is pushed inward. Pushing the knob 130 inward forces the rod 136 down the tube 132 to contact and push out the medial button 150 from the end of the tube 132, thereby deploying the medial button 150.

FIG. 28B shows that once the medial button 150 is deployed and flipped into place, the push buttons 124 can be further depressed and the knob 130 rotated until a hard stop is reached. The hard stop is created by interference of the keying features 128 of the knob 130 (shown in FIG. 13) with the flanges 116A, 116B of the handle 110. Rotation of the knob 130 at this position causes internal features of the knob 130 to couple around the retainer 134. At the hard stop, the knob 130 is pulled straight backward to remove the knob assembly 120 from the syndesmosis device inserter 100.

FIG. 28C shows that once the knob assembly 120 has been removed, two halves of the handle 110 can be twisted relative to each other to separate the two halves and release the lateral button 140 from the handle 110. With the two halves of the handle 110 separated as shown in FIG. 28D, each half of the handle 110 can be gripped and tensioning can be provided by pulling each strand of the suture 160 individually in line with the suture 160 between the medial button 150 and the lateral button 140. Once tensioned, the suture 160 is cut from the two halves of the handle 110. As a result, this method permits implantation of a syndesmosis device without a medial incision. Additionally, this method provides for pulling/tensioning of the suture 160 with the two halves of the handle 110 instead of using bare hands which can be painful and cuts gloves.

Figure 29:
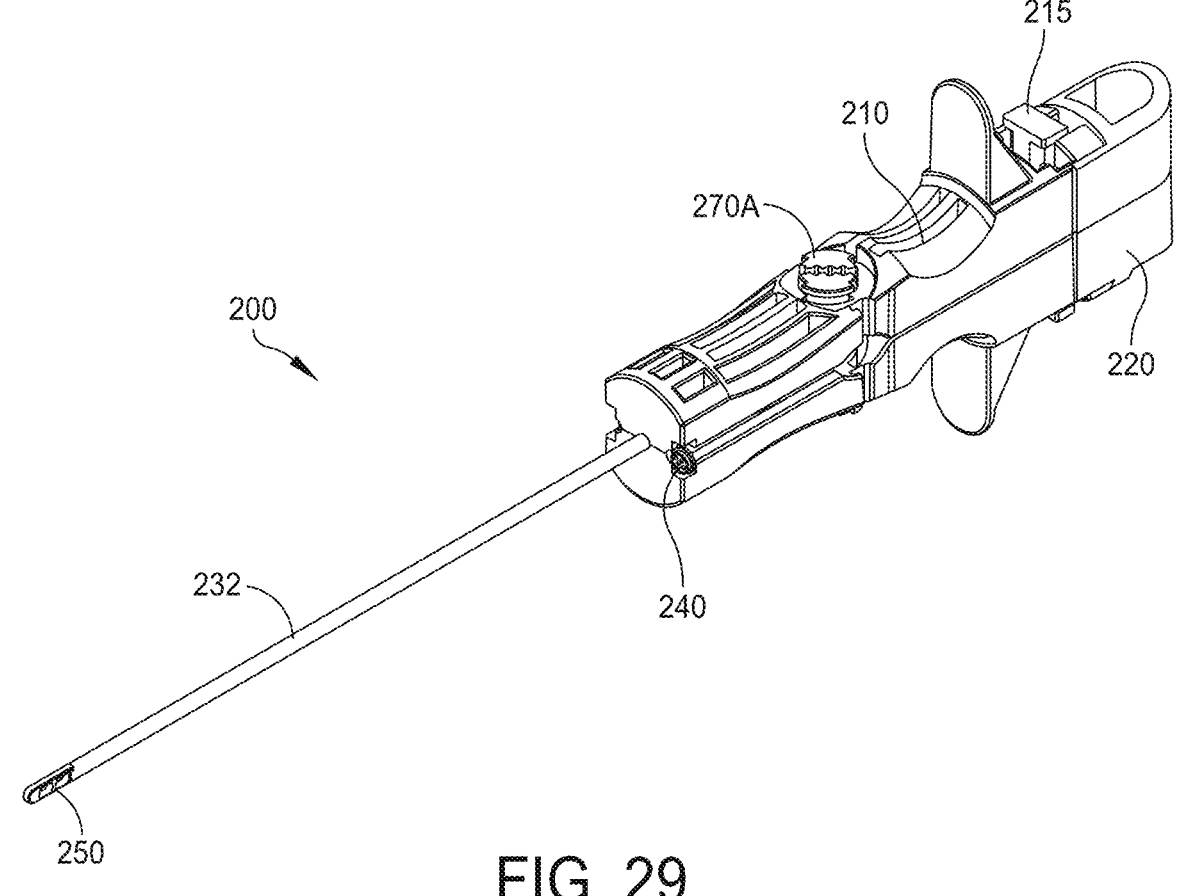
FIG. 29 is a perspective view of a syndesmosis device inserter according to another embodiment of the present disclosure.
Figure 30:
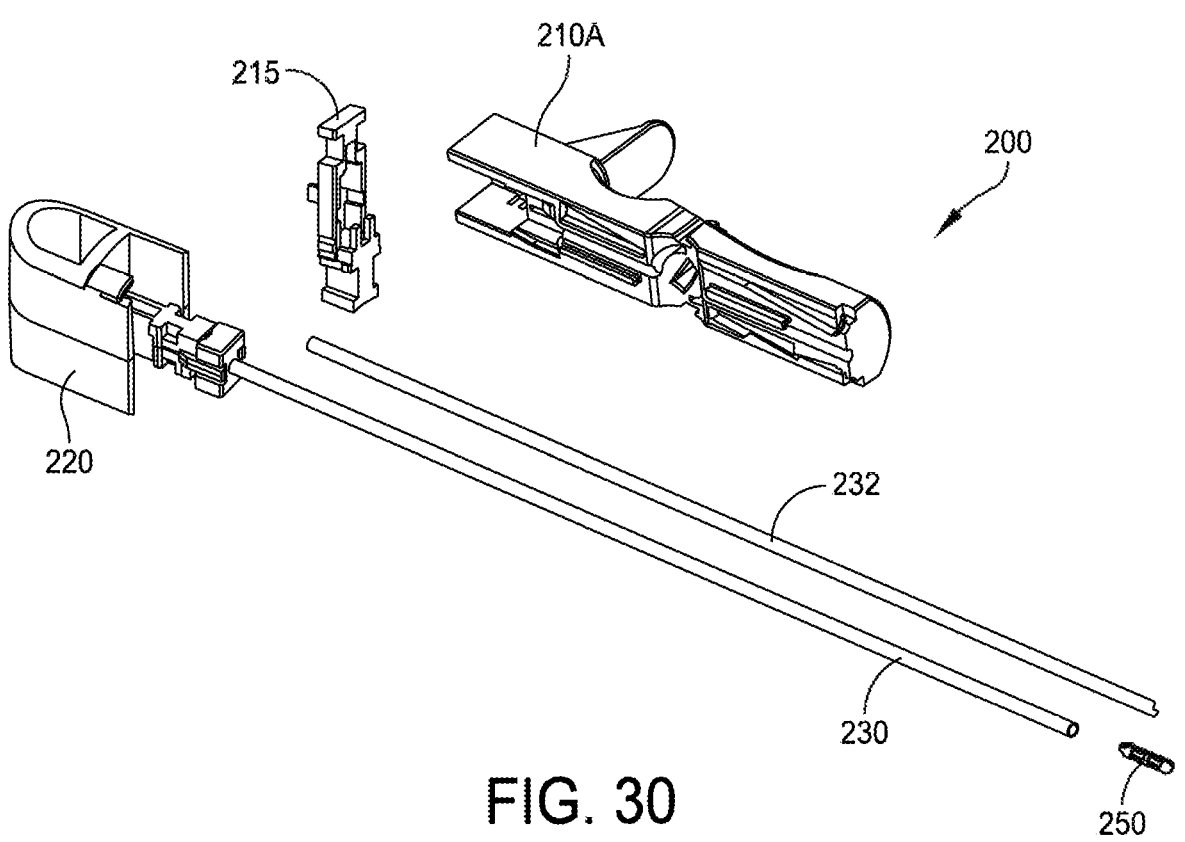
FIG. 30 is an exploded view of syndesmosis device inserter of FIG. 29.
Figure 30A:
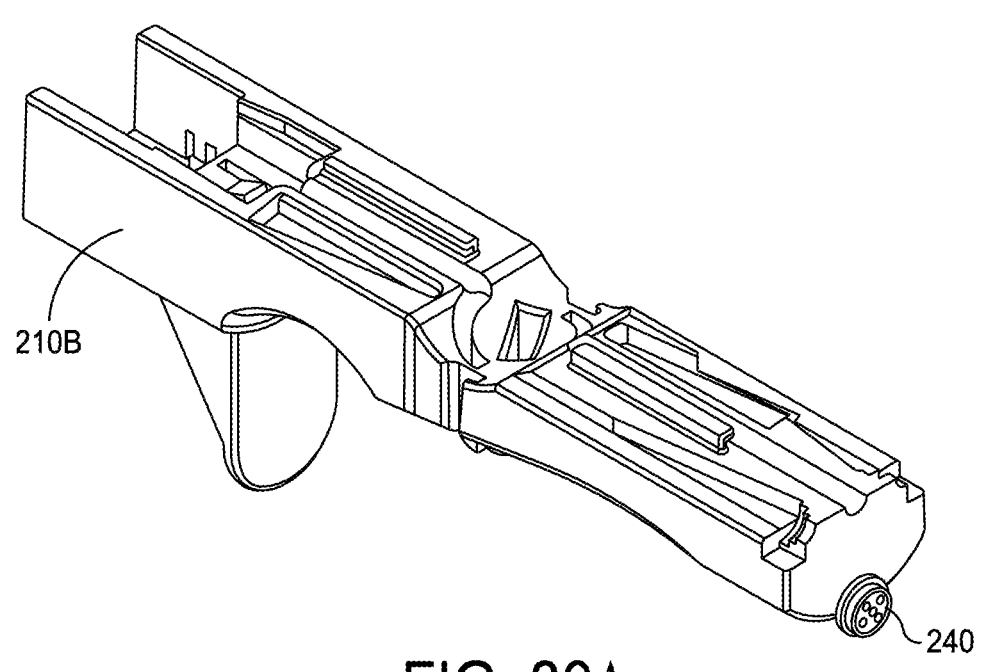
FIG. 30A presents the handle half from the exploded view of FIG. 30.

FIG. 29 is a perspective view and FIG. 30 is an exploded view of a syndesmosis device inserter 200 according to another embodiment of the current disclosure. As shown, the syndesmosis device inserter 200 can include a handle 210, a locking button 215, a pusher assembly 230, a tube 232, a lateral button 240, and a medial button 250. The lateral button 240 and the medial button 250 can be as previously described with respect to items 140 and 150, respectively.

As shown, in FIG. 30, the handle 210 can include two halves 210A and 210B where each half can include a corresponding suture post 270A and 270B as previously described.

Figure 31:
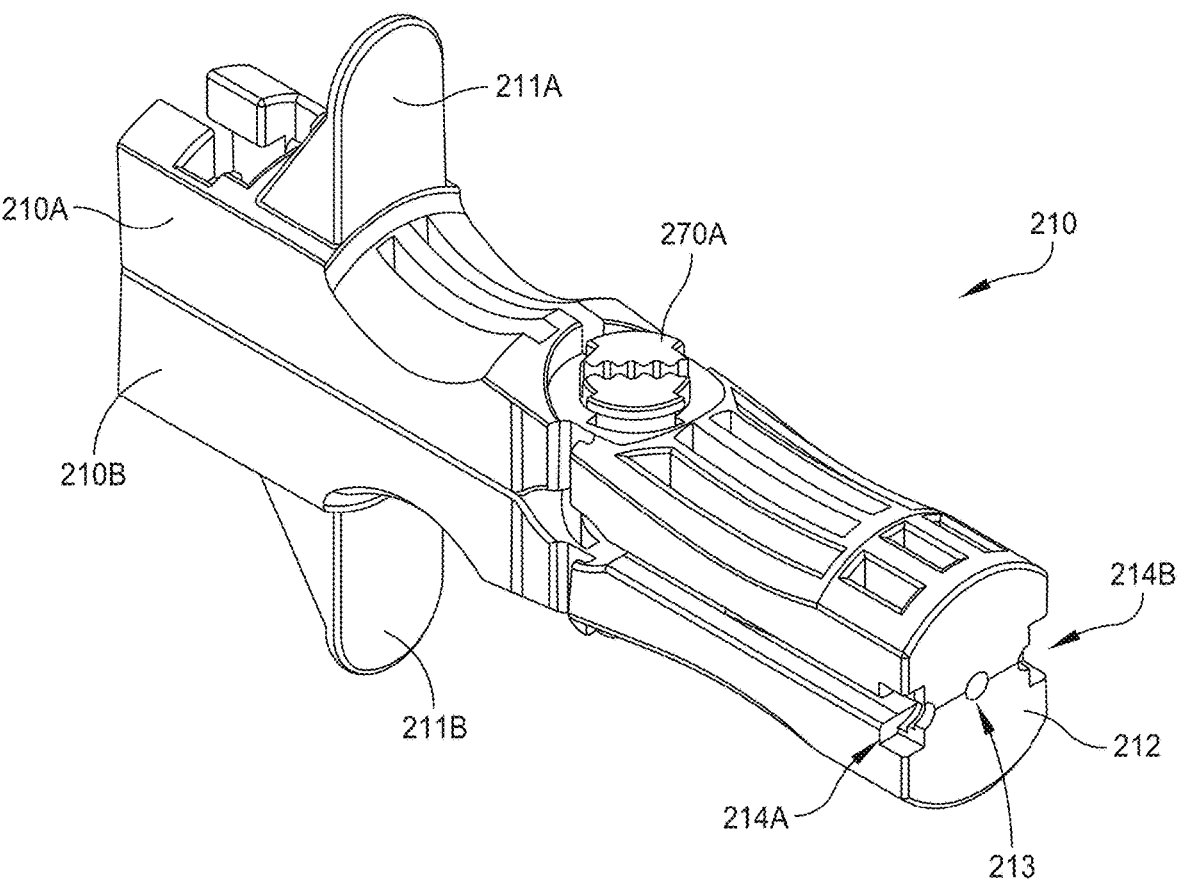
FIG. 31 and FIG. 32 are perspective views of a handle.
Figure 32:
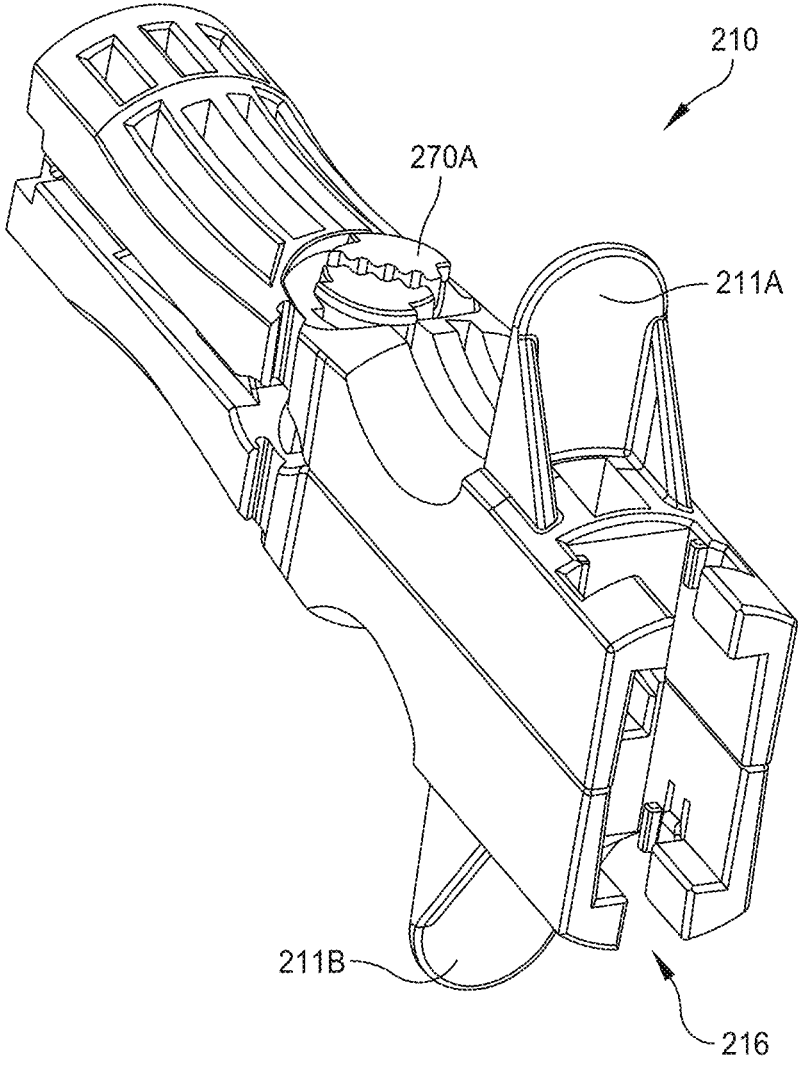

FIGS. 31 and 32 are perspective views of the handle 210. The handle 210 can include two halves 210A and 210B that when joined together to define a body that can be generally cylindrical. Each half 210A, 210B can include a finger grip 211A, 211B, respectively. Thus, a user can grip the handle 210 and use a syndesmosis device inserter 200 in which the handle 210 is a part with one hand. At a distal end 212, the handle 210 can include an opening 213 from which the tube assembly 230 can extend through. The distal end 212 can also include at least one groove 214A and 214B in which a lateral button 240 can be located. In an aspect, the distal end 212 can include two opposing grooves 214A and 214B. The grooves 214A, 214B can be sized and configured to accept a lateral button 240. Including more than one groove 214A/B provides a user flexibility to select a location in which to place the lateral button 240 as desired to fit the surgery.

FIG. 32 is a perspective view of a proximal end 216 of the handle 210. The proximal end 216 can include a cutout and features used to retain the pusher assembly 230, and the locking button 215.

Figure 33:
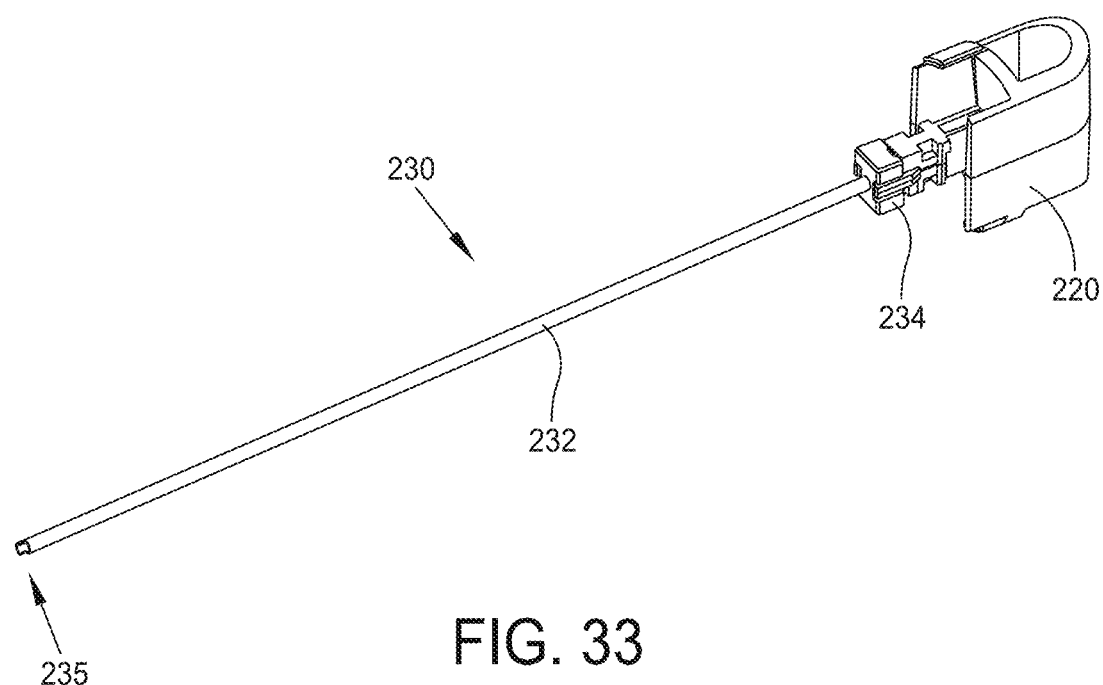
FIG. 33 is a perspective view of a tube assembly.

FIG. 33 is a perspective view of the pusher assembly 230 with some features as previously described. As shown, the pusher assembly 230 can include a cannulated tube 232 that includes a cutout portion defining a notch 235 at one end of the tube 232, a retainer 234, and a pusher 220. The rod 236 can be integrally define with the pusher 220 via overmolding or another technique and is covered and not visible in FIG. 33 The notch 235 can be used to retain the medial button 250 that can be press fit into the notch 235. The retainer 234 can be force fit over an end of the rod 236 or integrally defined with the pusher 220 and the rod 236. The retainer 234 can include geometric features used to mate with and be secured by features of inner portions of the handle 210. The rod 236 fits into a lumen or bore of the tube 232 and extends from an end of the tube 232 and is moveable to be slid into tube 232.

Figure 34:
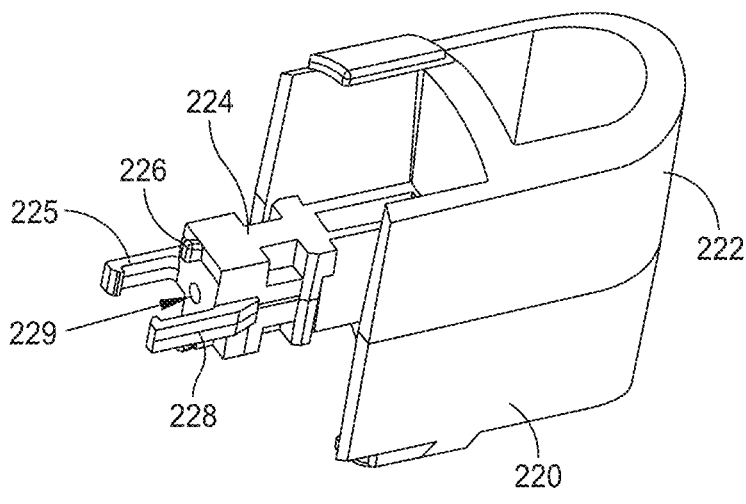
FIG. 34 is a perspective view of a pusher.

FIG. 34 is a perspective view of the pusher 220. As shown, the pusher 220 can include a U-shaped body 222 with a rounded portion at one end. The pusher 224 can also include an extending portion 224 that includes two release tabs 225, and a claw or grip 226 at one end that can include two opposing tabs 228. The extending portion 224 can also include a hole 229 in which the rod 236 fits into. The extending portion 224 can include geometric features suitable for coupling and communication with the locking button 215. The claw 226 is configured to be coupled with the retainer 234 as described below.

Figure 35:
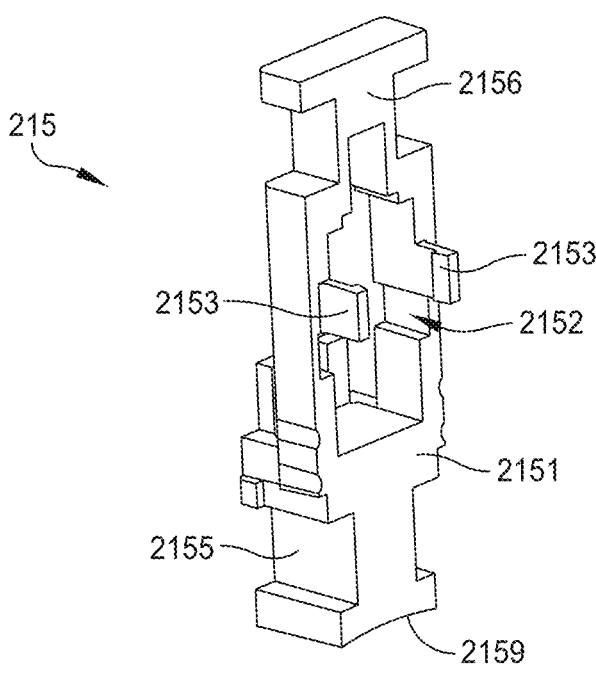
FIG. 35 and FIG. 36 are perspective views of a locking button.
Figure 36:
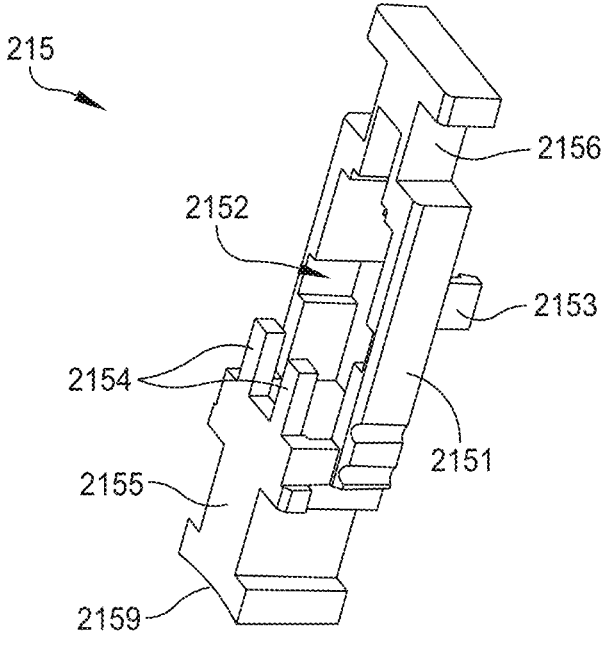

FIGS. 35 and 36 are perspective views of the locking button 215. The locking button 215 can include a body 2151 with an opening 2152 therethrough. Geometric features of the body 2151 defining the opening 2152 permit the extending portion 224 of the pusher 220 to fit through the opening 2152, as discussed in more detail below. One side of the body 2151 can include two opposing capture tabs 2153 extending from the body 2151. The opposite side of the body 2151 can include two locking tabs 2154 that are offset a distance from the body 2151 and extend in a direction parallel longer sides of the body 2151. Two opposing ends of the body 2151 can include T-shaped portions 2155 and 2156 that extend from the body 2151 with the top leg of the T-shape being parallel to shorter sides of the body 2151. A concave surface 2159 at the top leg of the T-shaped portion 2155 can be used to push on the locking button 215 while assembled in the syndesmosis device inserter 200 to unlock the pusher 220 from being removable.

Figure 37:
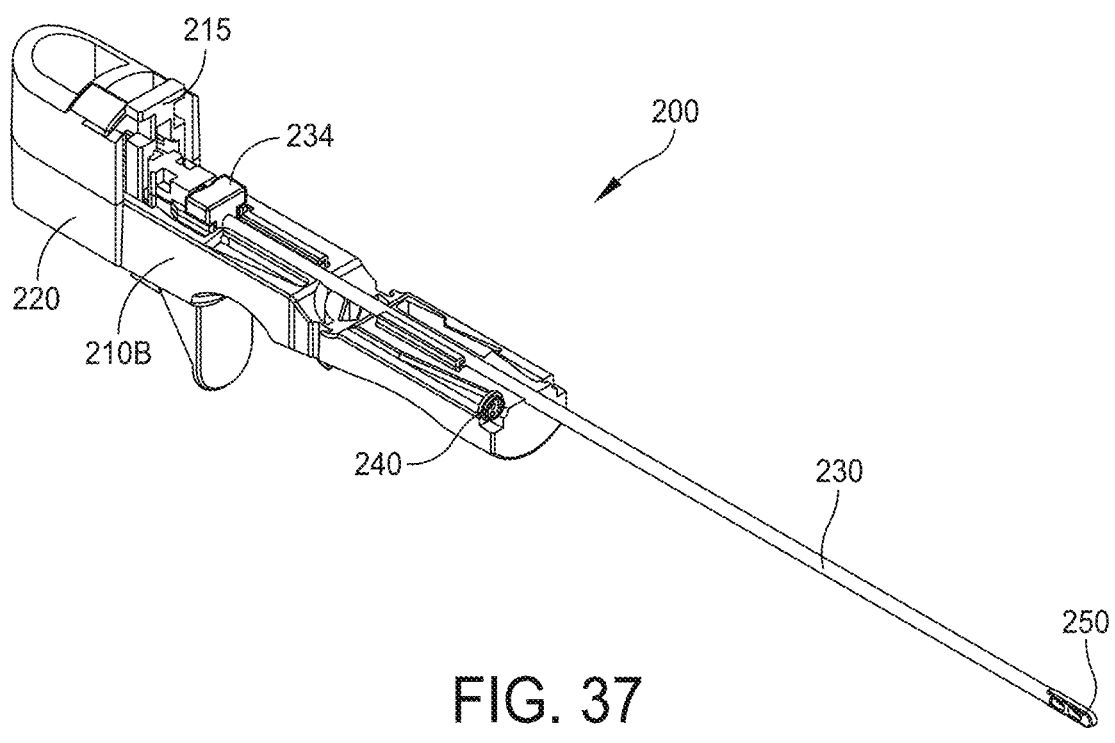
FIG. 37 is a perspective view of a syndesmosis device inserter with one half of the handle removed.
Figure 38:
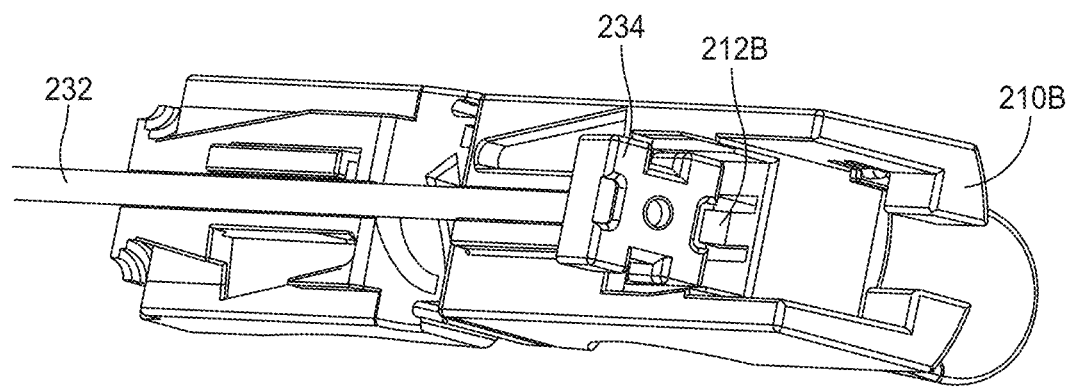
FIG. 38 is a perspective view showing an arrangement of a tube and a retainer assembled within one half of the handle.

FIG. 37 is a perspective view of the syndesmosis device inserter 200 with one half 210A of the handle 210 removed. This view shows an internal arrangement of one half of the housing 210B, the pusher assembly 230 with retainer 234, and the locking button 215. FIG. 38 is a perspective view showing an arrangement of the tube 232 and the retainer 234 assembled within one half of the handle 210B. The retainer 234 can be snapped or locked into place in the handle 210B via a tab 212B.

Figure 39:
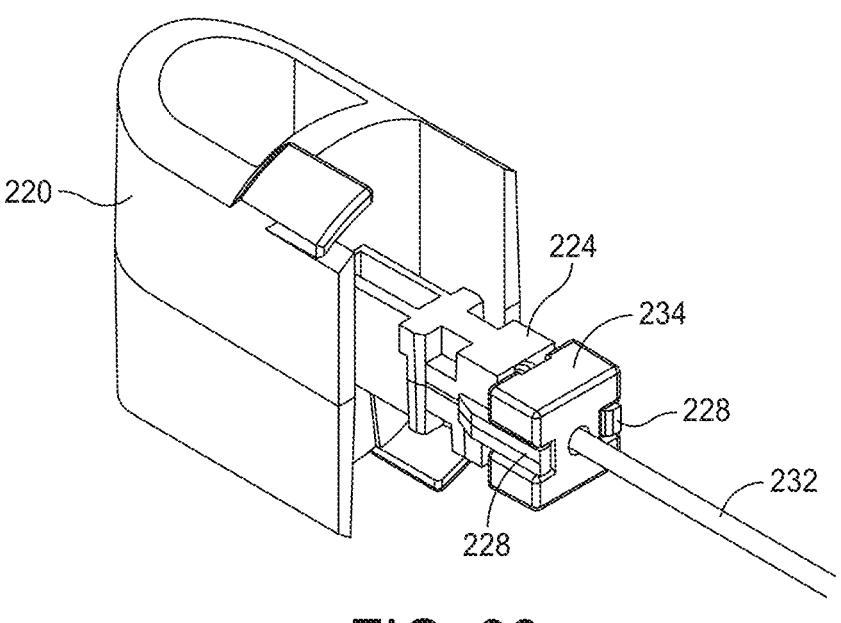
FIG. 39 is a perspective view showing an arrangement including the tube assembly and the pusher.

FIG. 39 is a perspective view showing an arrangement including the tube assembly 230 and the pusher 220. As shown, the tube assembly 230 can be arranged such that the rod 236 is fit into the hole 229 (not visible) of the pusher 220 and the two opposing tabs 228 of the pusher 220 fit around the retainer 234 to secure the tube assembly 230 and the pusher together. However, before the pusher 220 and the tube assembly 230 are arranged in this manner, the extending portion 224 of the pusher 220 is fit through the opening 2152 of the locking button 215, as shown in FIG. 40.

Figure 40:
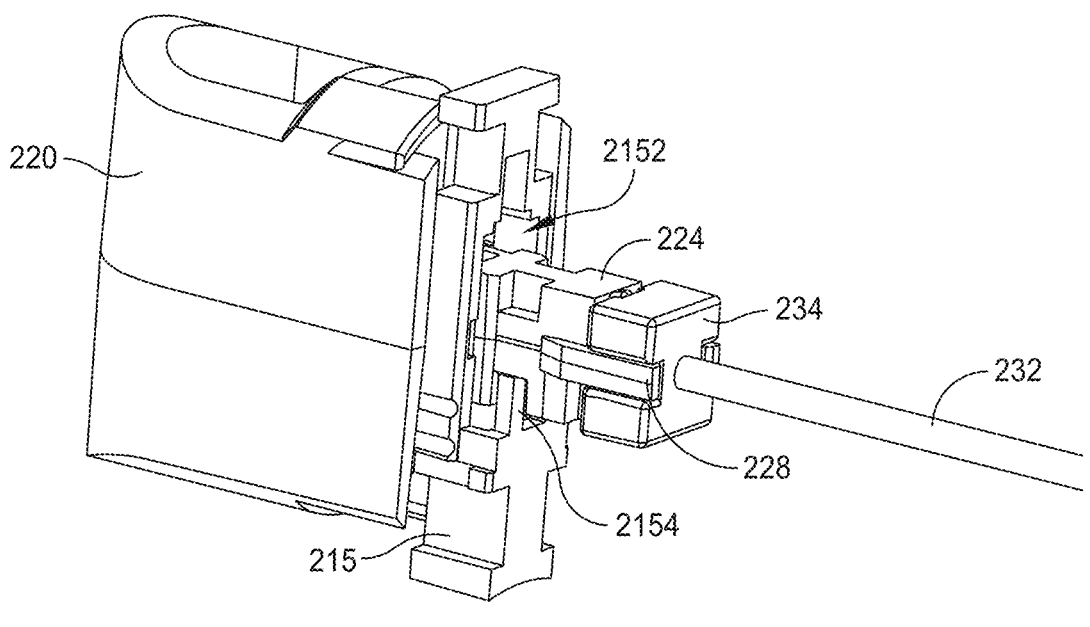
FIG. 40 is a perspective view showing an arrangement of the pusher, the locking button, and the tube assembly.

FIG. 40 is a perspective view showing an arrangement of the pusher 220, the locking button 215, and the tube assembly 230. As shown, the opening 2152 is larger than the extending portion 224 such that the locking button 215 can be slid up and down along the extending portion 224. In the position as shown, the locking button 215 is in the hard-stop position where the locking tabs 2154 are fit into a groove of the extending portion 224 blocking the locking button 215 from further traveling vertically upward in the orientation shown. In this position, the pusher 220 and the locking button 215 are locked together.

Figure 41:
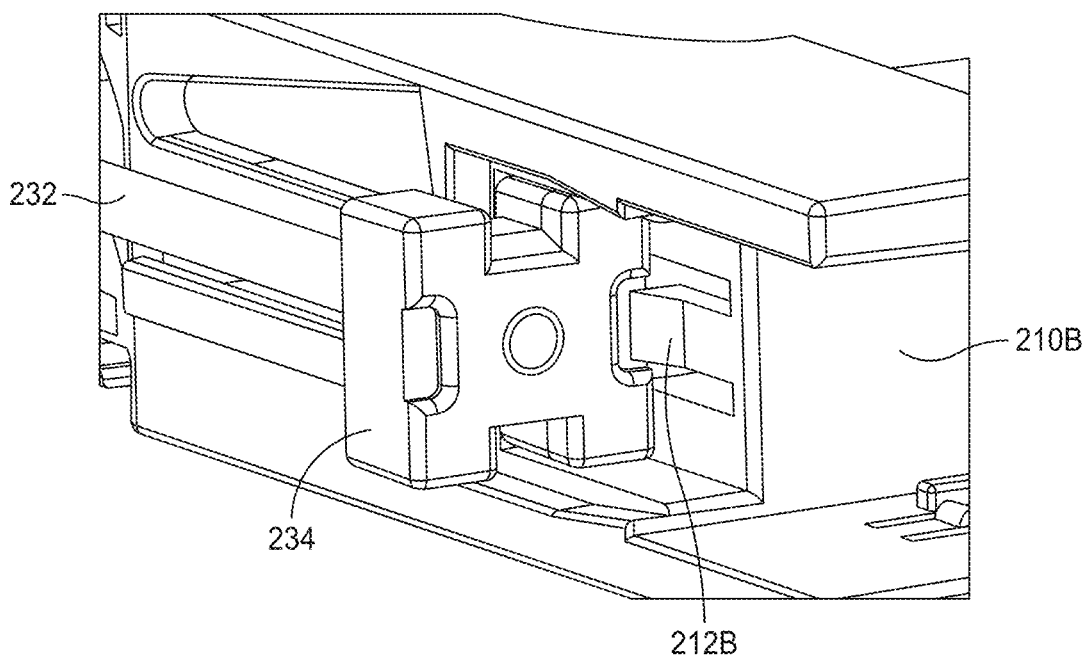
FIG. 41 to FIG. 45 show how the syndesmosis device inserter can be assembled.
Figure 42:
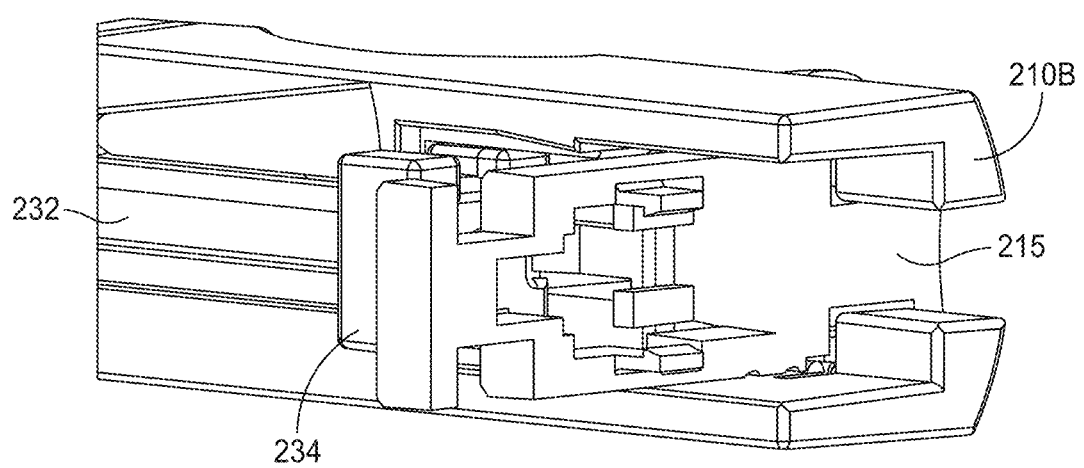
Figures 43, 44:
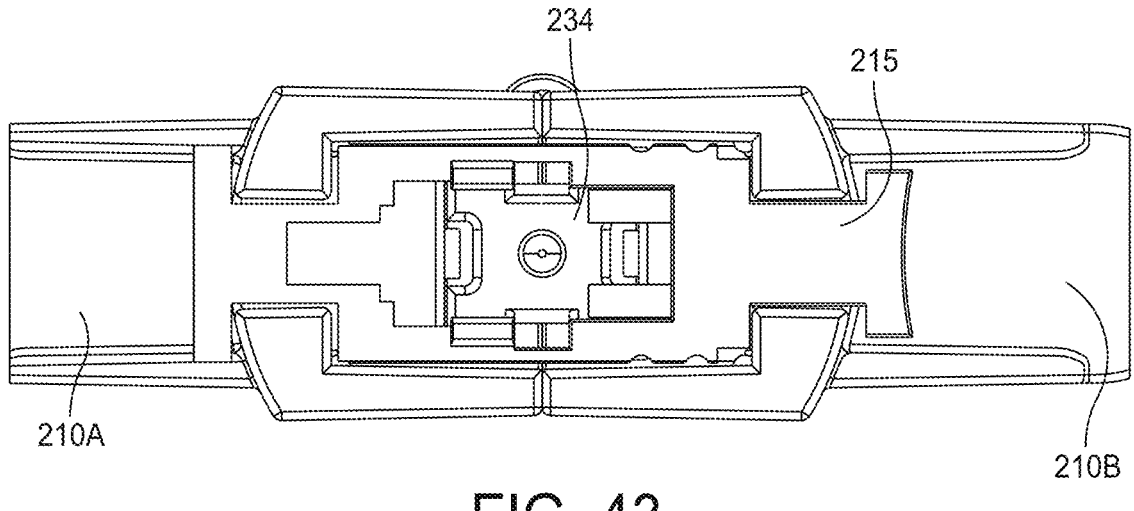
Figure 45:
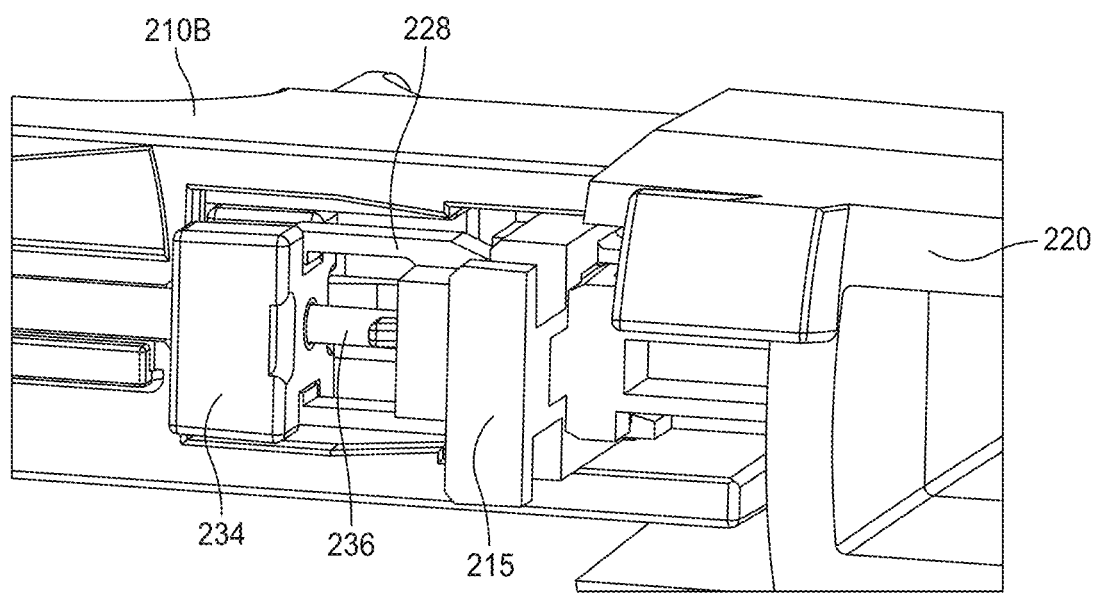

FIGS. 41 to 45 show how the syndesmosis device inserter 200 can be assembled. FIG. 41 shows that the retainer 234 with tube 232 can be snapped into one side of the handle 210B via retention tab 212B. Next, FIG. 42 shows that the locking button 215 can be is slid into place in the one side of the handle 210B. FIG. 43 is a rear view showing the locking button 215 in place with both sides of the handle 210A and 210B. Next, FIG. 44 shows the pusher 220 and rod 236 slid into place where the rod 236 is aligned with the tube 232. FIG. 45 shows that in this state the locking button 215 holds the pusher 220 in place and the retainer 234 is held in place with the retention tab 212B built into the one side of the handle 210B. In this state, the syndesmosis device inserter 200 is ready to use.

Figure 46:
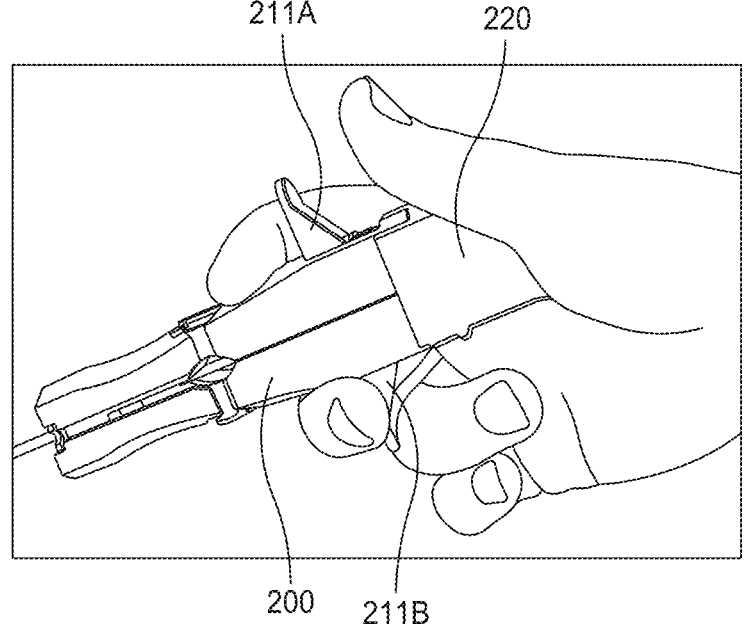
FIG. 46 shows how a syndesmosis device inserter can be gripped with one hand during use.

FIG. 46 shows how the syndesmosis device inserter 200 can be gripped with one hand during use. The index and middle finger of one hand can be located for leverage around the finger grips 211A and 211B and the pusher 220 can be pushed with on the palm while the thumb can push the locking button 215 (not shown).

FIGS. 47-52 show how the syndesmosis device inserter 200 can be used during a surgical technique, for example during ankle surgery. In use during surgery, after an incision is made on the lateral side of the ankle and a hole is drilled from the lateral side of the fibula 271 through the tibia 272, the medial button 250 and suture construct is inserted first, through the hole made in the fibula 271 and then through both cortices of the tibia 272 until the tube 232 is flush to the medial cortex of the tibia 272. Once the medial button 250 is beyond the medial cortex of the tibia 272 and fully exited the tibia 272, the locking button 215 is pushed to the hard-stop position to release the pusher 220.

Figure 50:
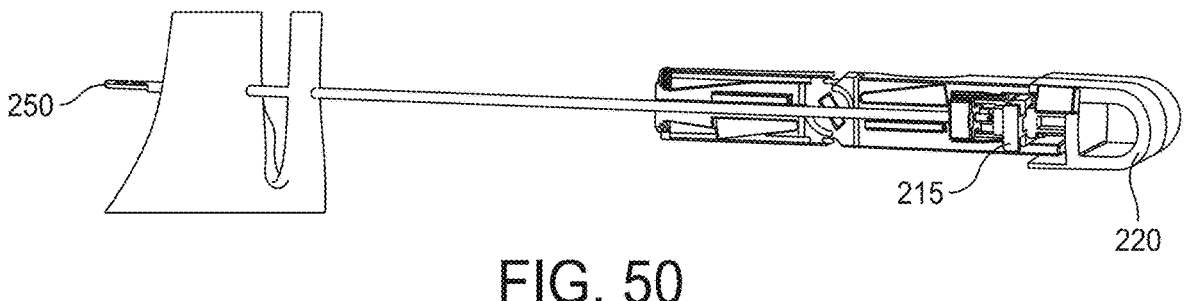
Figure 51:
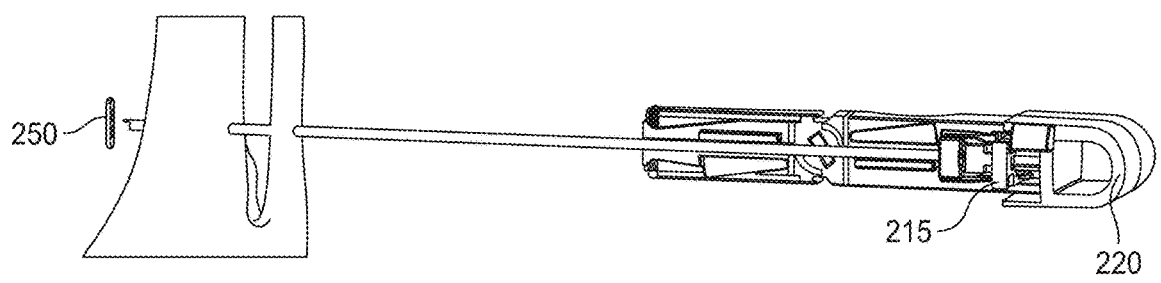

FIG. 48 shows the locking button 215 in the locked state. Once the locking button 215 is released, as shown in FIG. 49, the pusher 220 can be depressed to force the rod 236 forward to release the medial button 250. FIG. 50 shows the locking button 215 is the released state and the pusher 220 in the pre-deployment position. FIG. 51 shows that once the pusher 220 is pushed forward the medial button 250 has flipped after being deployed under the patient's skin.

Figure 52:
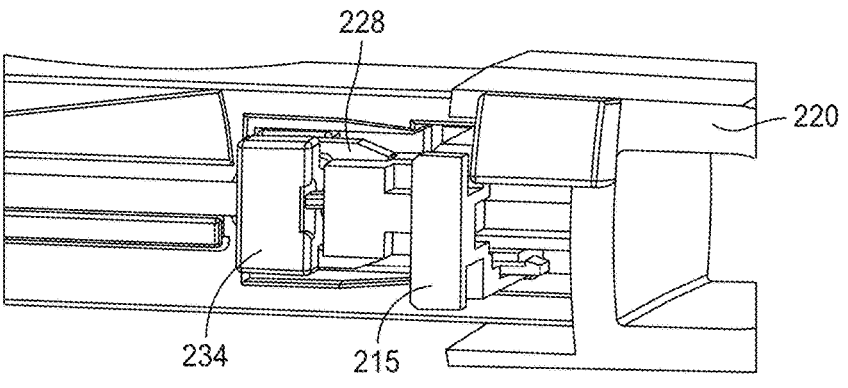
Figure 53:
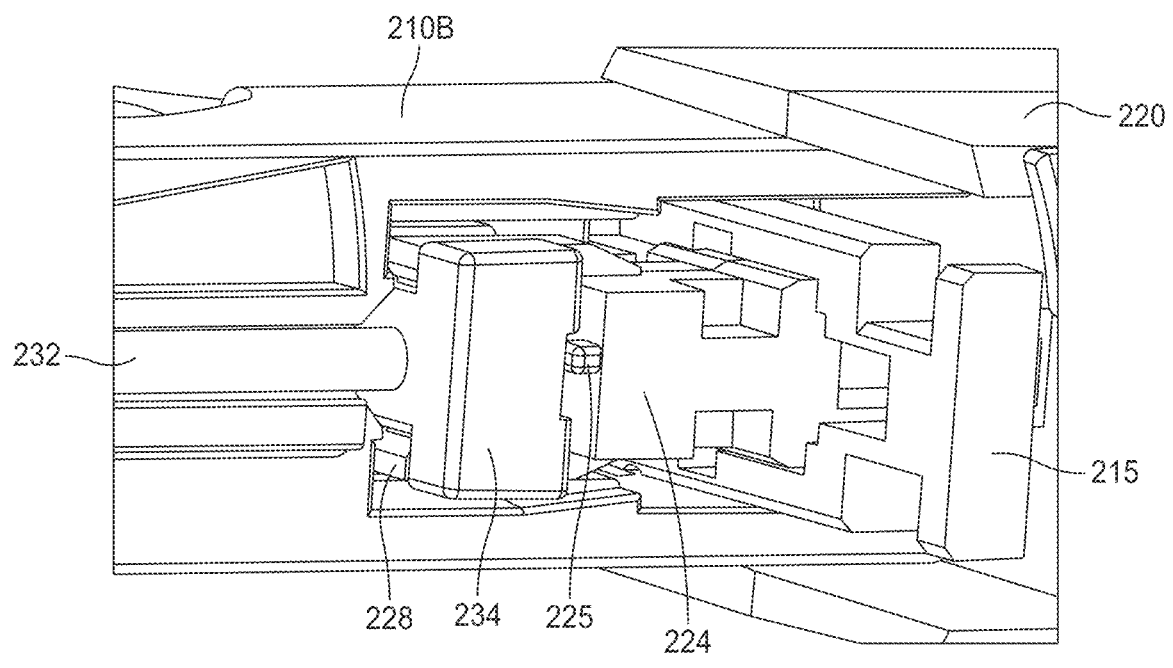
Figure 54:
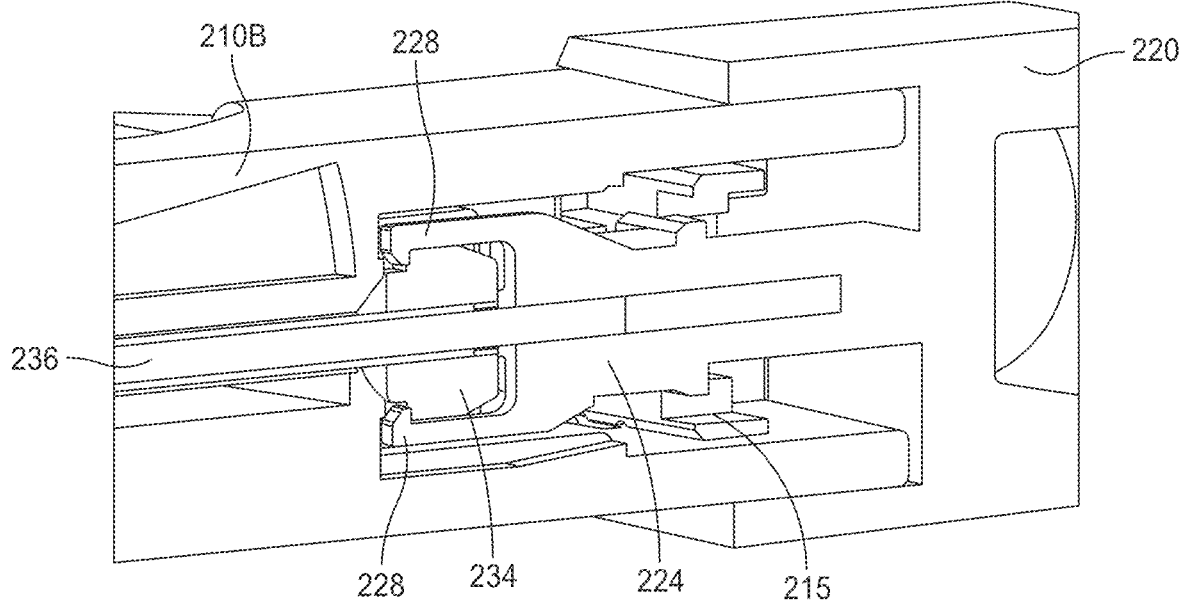
Figure 55:
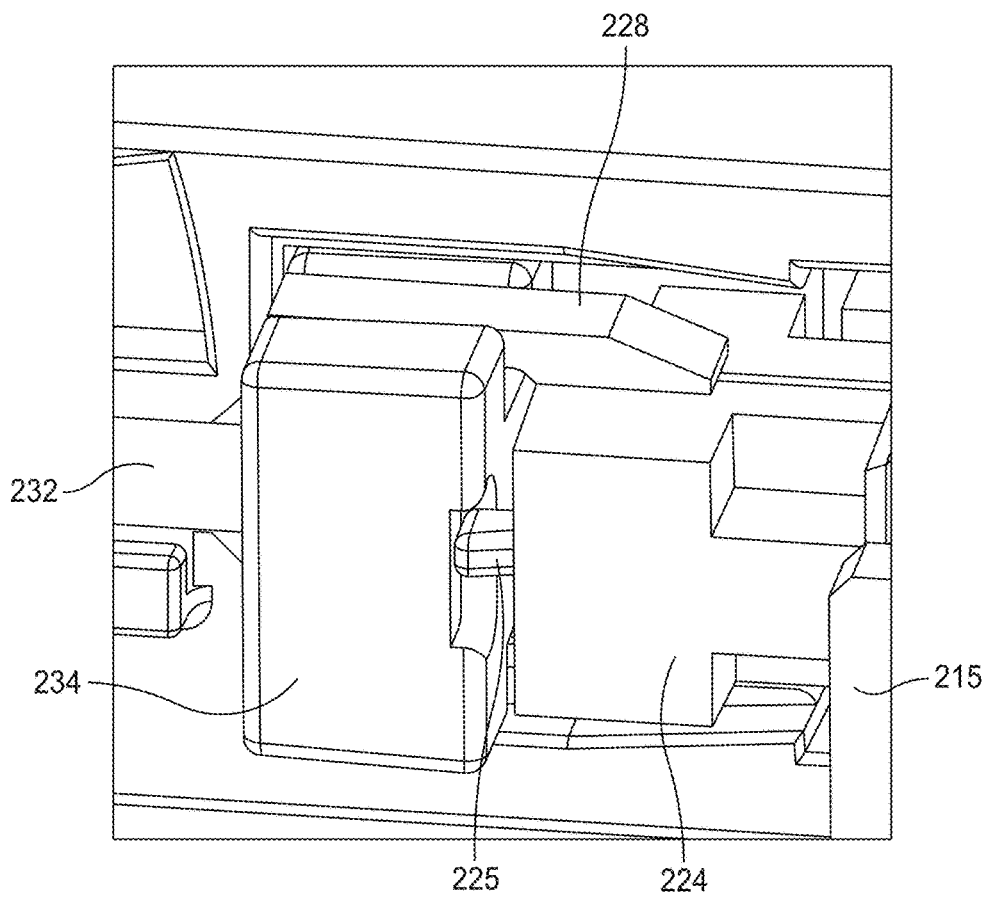
Figure 56:
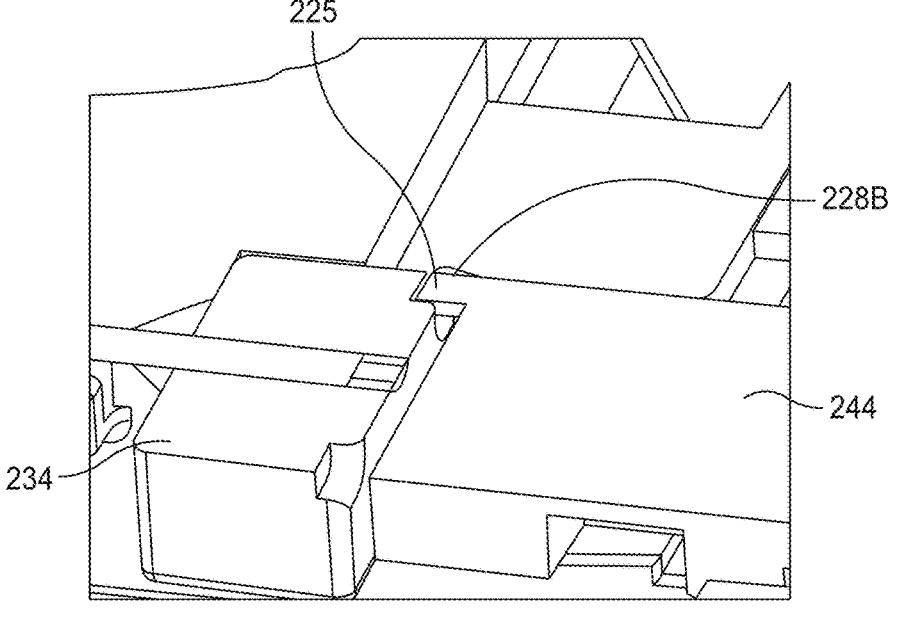

FIGS. 52 to 54 show that once the pusher 220 is pushed forward it locks onto the retainer 234 of the tube assembly 230 via the two opposing tabs 228. In this state the locking button 215 once again locks the pusher 220 that is now attached to the tube assembly 230. FIG. 55 is a close up view showing that during the pressing of the pusher 220 the two release tabs 225 (one being shown circled in red) press the tube assembly retention tabs 228A, 228B out of the way allowing the tube assembly 230 to be released. A cross section showing a release tab 225 pushing a retention tab 228B is shown in FIG. 56. At this point the locking button 215 is pushed again to release the internal components (i.e., the tube assembly 230, the locking button 215, and the pusher 220) from the handle 210. These components are then pulled out the rear of the handle 210.

Figure 57:
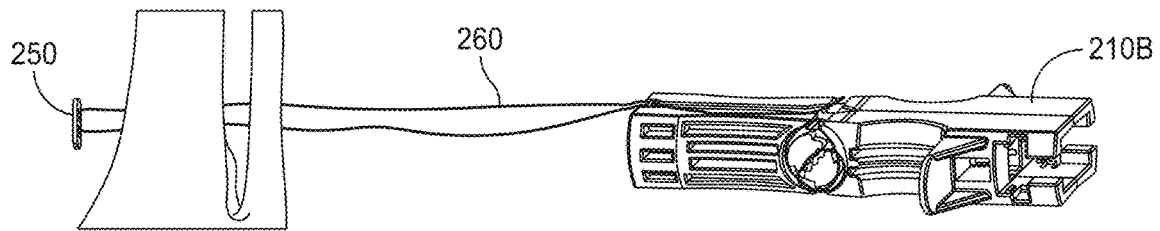
Figure 58:
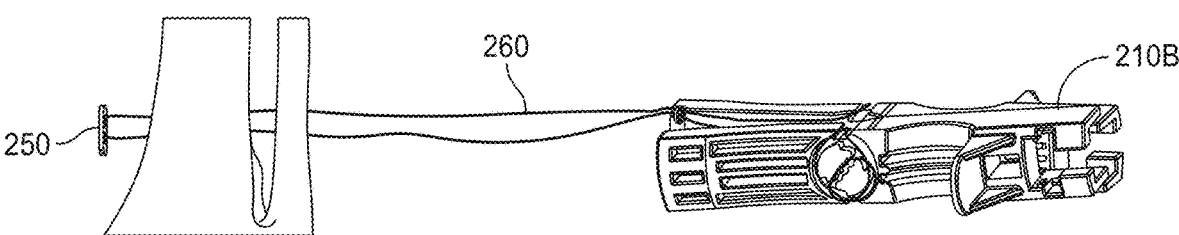
Figure 59:
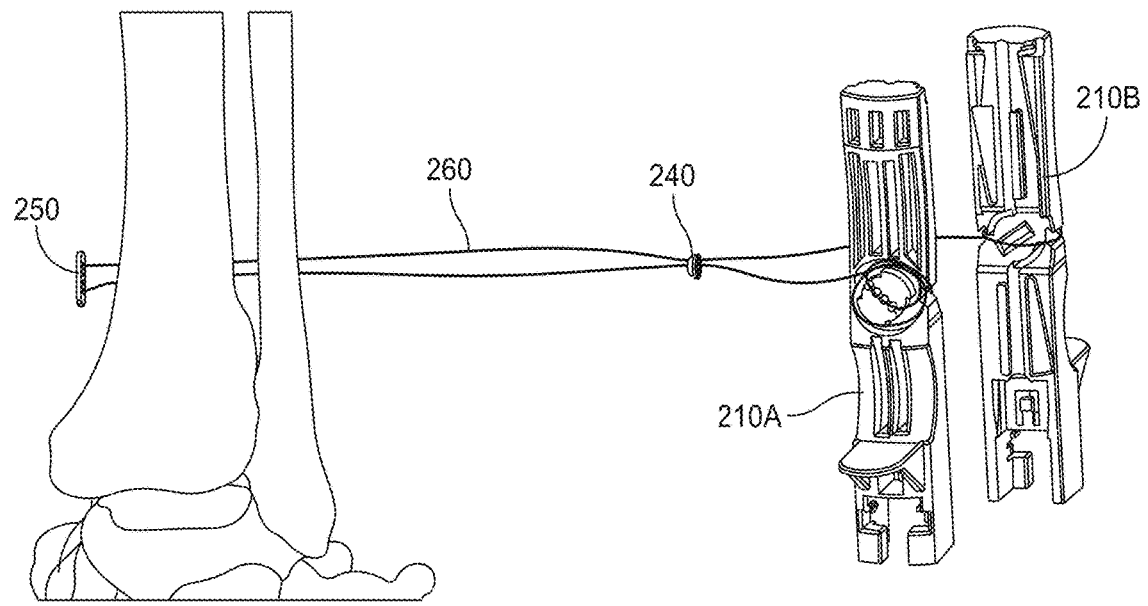

FIGS. 57 to 59 show that once the internal components have been removed, two halves of the handle 210A, 210B can be twisted relative to each other to separate the two halves and release the lateral button 240 from the handle 210. With the two halves of the handle 210A, 210B separated as shown in FIG. 59, each half of the handle 210 can be gripped and tensioning can be provided by pulling each strand of the suture 260 individually in line with the suture 260 between the medial button 250 and the lateral button 240. Once tensioned, the suture 260 is cut from the two halves of the handle 210A, 210B. As a result, this method permits implantation of a syndesmosis device without a medial incision using one hand. Additionally, this method provides for pulling/tensioning of the suture 260 with the two halves of the handle 210 instead of using bare hands which can be painful and cuts gloves.

FIG. 60 to FIG. 63 are views showing a syndesmosis device inserter 300 according to another embodiment of the present disclosure. This embodiment is similar to that shown and described with respect to FIG. 29 but includes a safety cover 317.

Figure 60:
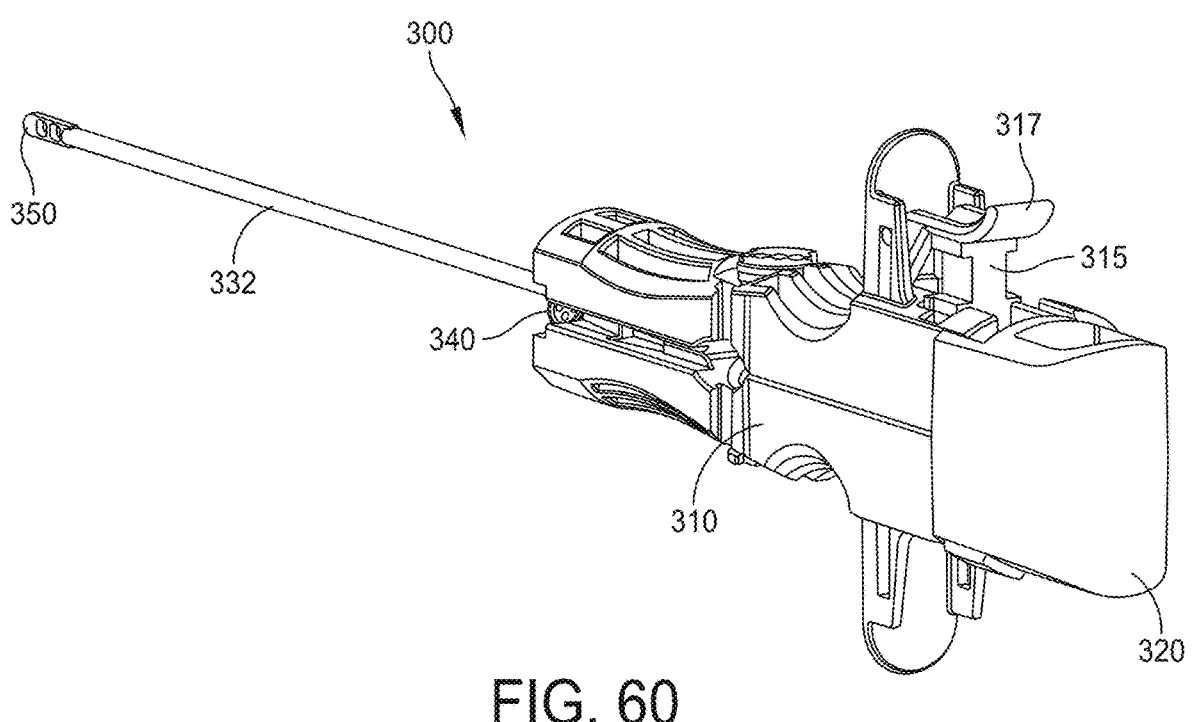
FIG. 60 to FIG. 63 are views of a syndesmosis device inserter according to another embodiment of the present disclosure.

FIG. 60 is a perspective view of a syndesmosis device inserter 300 according to another embodiment of the current disclosure. As shown, the syndesmosis device inserter 300 can include a handle 310, a locking button 315, a safety cover 317, a pusher assembly 330, a tube 332, a lateral button 340, and a medial button 350. Description of components previously provided are omitted for brevity.

Figure 61:
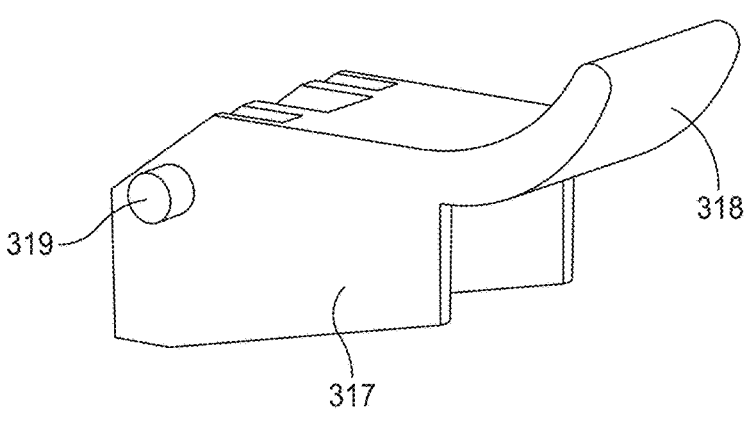
Figure 62:
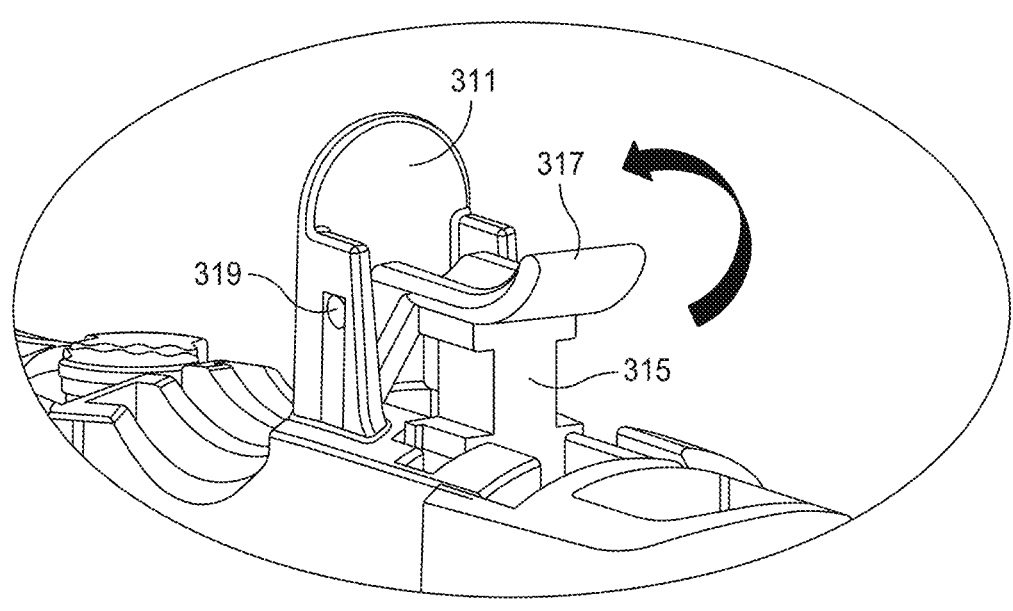
Figure 63:
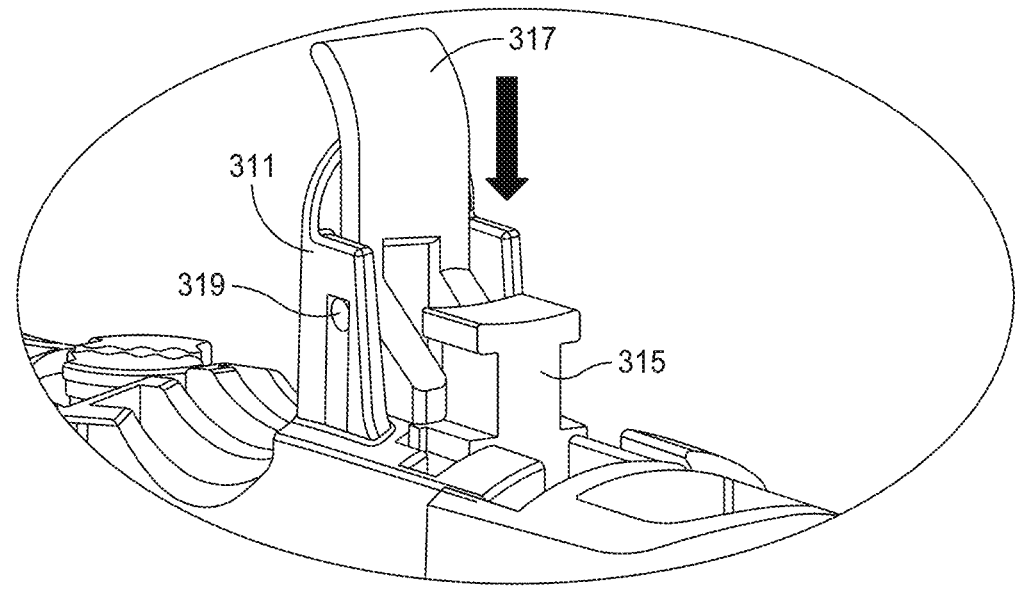

FIG. 61 is a perspective view of the safety cover 317 showing that the safety cover 317 can include a cantilevered portion 318 and two bosses 319, one on each side of the safety cover 317. As shown in FIG. 60, the safety cover 317 covers the locking button 315 so that the surgeon cannot push the locking button 315 without moving the safety cover 317 and deploy the syndesmosis device inserter 300 inadvertently. As shown in FIGS. 62 and 63, when the surgeon is ready to deploy the syndesmosis device inserter 300, the surgeon can flip the safety cover 317 up out of the way with their thumb. When they do that, the bosses 319 on the sides of the safety cover 317 slide down in corresponding slots of the finger grip 311 so that the safety cover 317 stays out of the way and does not interfere with depressing the locking button 315 to release the pusher assembly 330.

Figure 64:
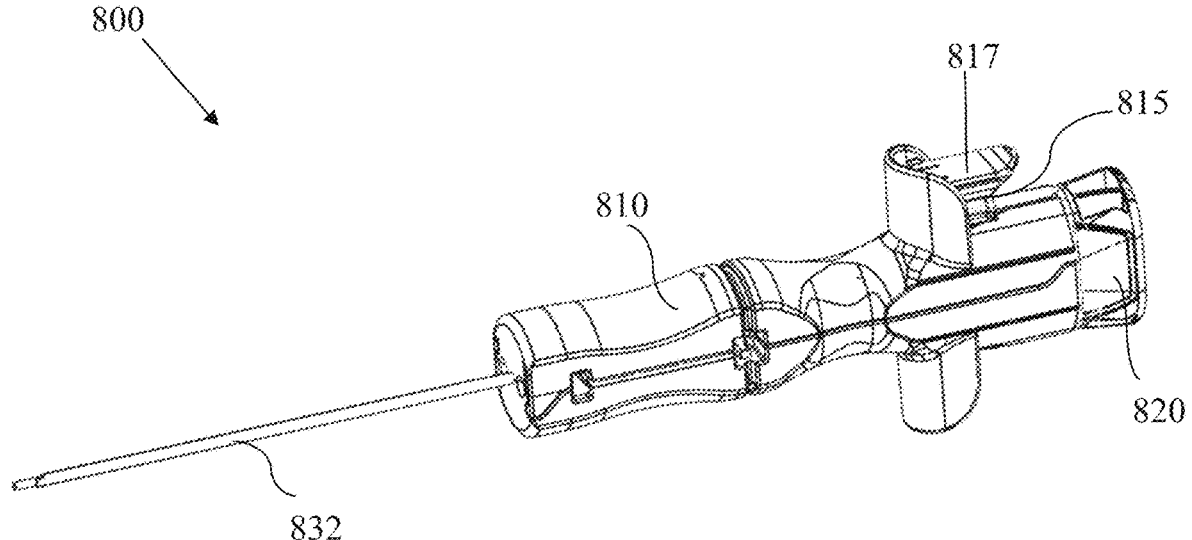
FIG. 64 is a perspective view of a syndesmosis device inserter according to another embodiment of the present disclosure.
Figure 65:
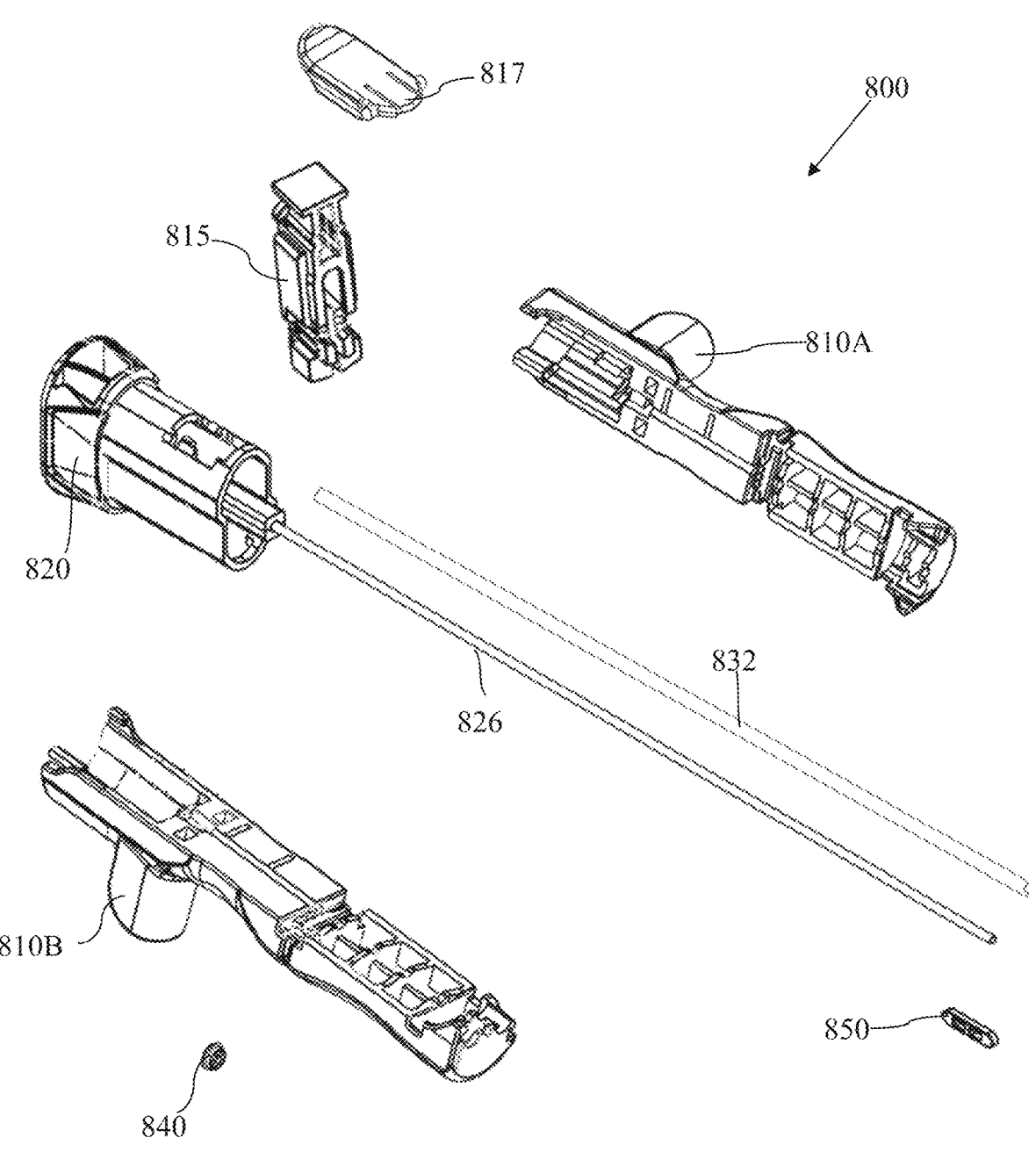
FIG. 65 is an exploded view of syndesmosis device inserter of FIG. 64.

The pusher assembly 330 of the syndesmosis device inserter 300 operates the same as the pusher assembly 220 of the syndesmosis device inserter 200, described above. That is, depressing the locking button 315 releases the pusher assembly 220, which when squeezed using the two finger tabs 311 and palm to deploy the medial button 350. After the medial button 350 is deployed, the locking button 315 is pushed again to release the internal components. Then, the pusher assembly 320 is pulled back removing the internal components. When the pusher assembly 320 with internal components are removed, the handle FIG. 64 is a perspective view and FIG. 65 is an exploded view of a syndesmosis device inserter 800 according to another embodiment of the current disclosure. This syndesmosis device inserter 800 includes some features previously described, descriptions of which can be omitted for brevity. As shown, the syndesmosis device inserter 800 can include a handle 810, a locking button 815, a safety cover 817, a grip assembly 830 including a grip 820, a rod 826, and a tube 832, a lateral button 840, and a medial button 850.

Figure 66:
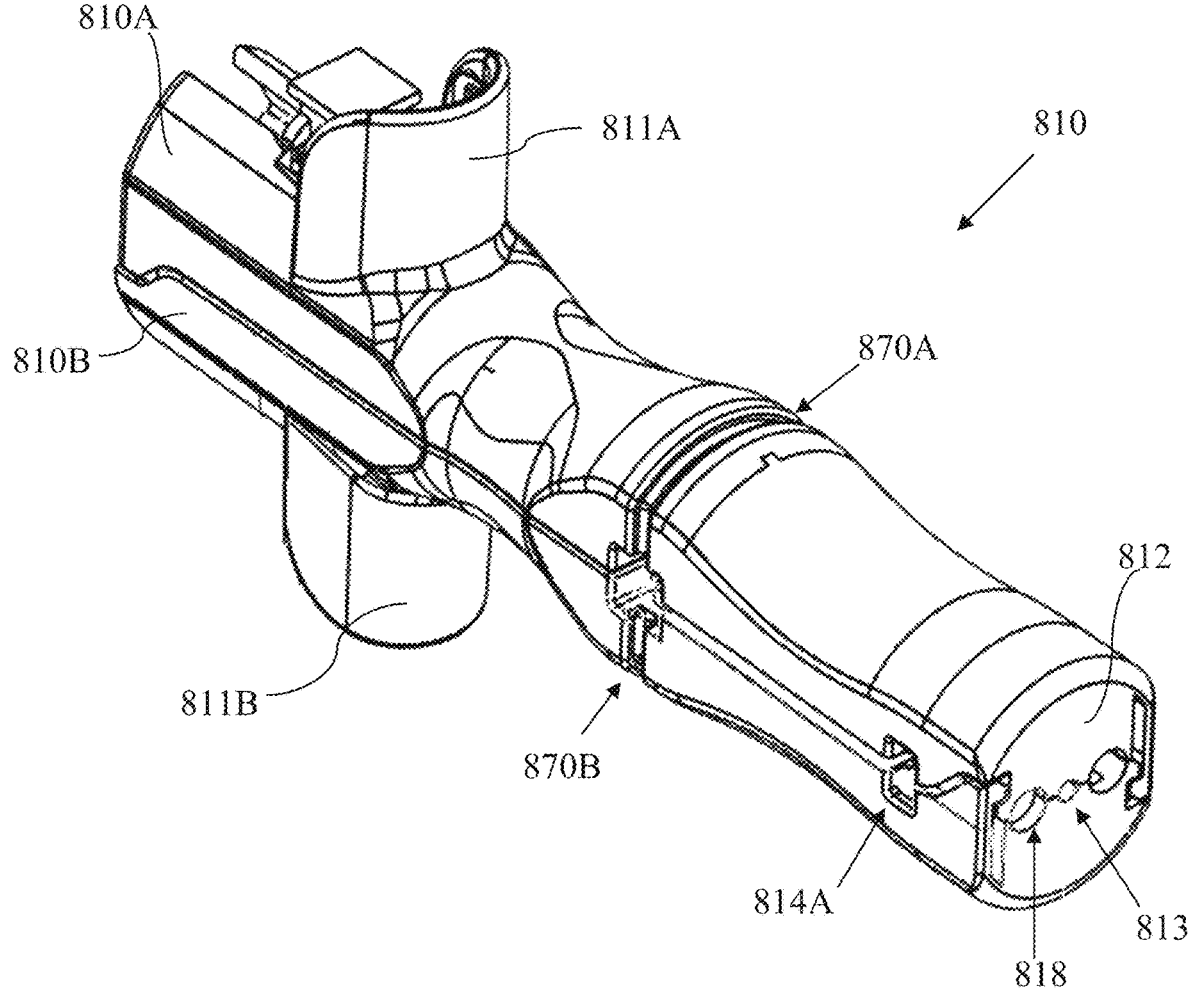
FIG. 66 and FIG. 67 are perspective views of a handle.

As shown, in FIG. 65, the handle 810 can include two halves 810A and 810B where each half can include a corresponding suture groove 870A/870B (viewable in FIG. 66).

Figure 67:
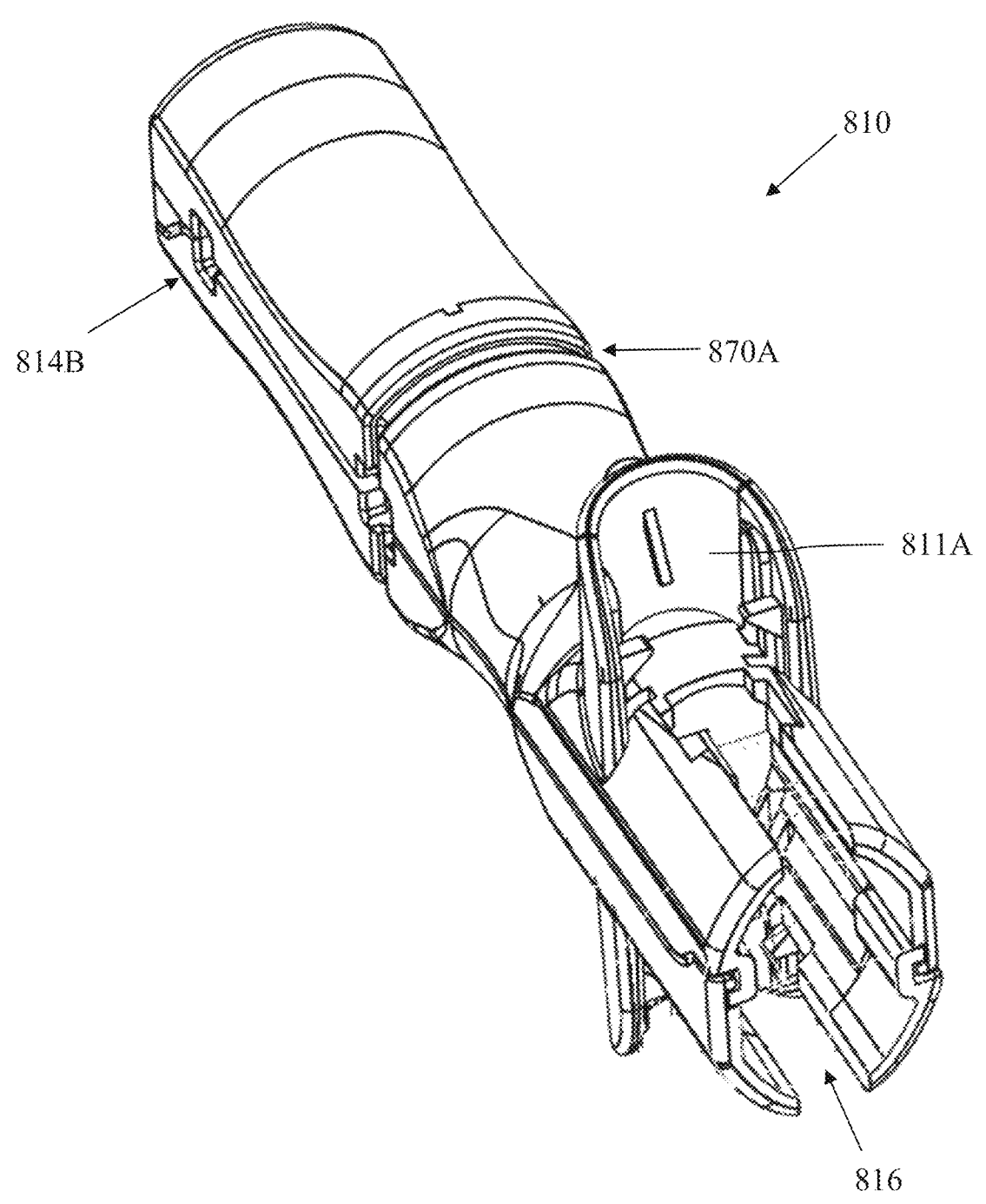

FIGS. 66 and 67 are perspective views of the handle 810. The handle 810 can include two halves 810A and 810B that when joined together define a body that can be generally cylindrical. Each half 810A, 810B can include a finger grip 811A, 811B, respectively. Thus, a user can grip the handle 810 and use the syndesmosis device inserter 800 in which the handle 810 is a part with one hand. At a distal end 812, the handle 810 can include an opening 813 from which the grip assembly 830 can extend through and two suture holes 818 in which a suture can pass through. The distal end 812 can also include at least one groove 814A and 814B in which a lateral button 840 can be located. In an aspect, the distal end 812 can include two opposing grooves 814A and 814B. The grooves 814A, 814B can be sized and configured to accept a lateral button 840. Including more than one groove 814A/814B provides a user flexibility to select a location in which to place the lateral button 840 as desired to fit the surgery.

FIG. 67 is a perspective view of a proximal end 816 of handle 810. The proximal end 816 can include a cutout and features used to retain the grip assembly 830, and the locking button 815.

Figure 68:
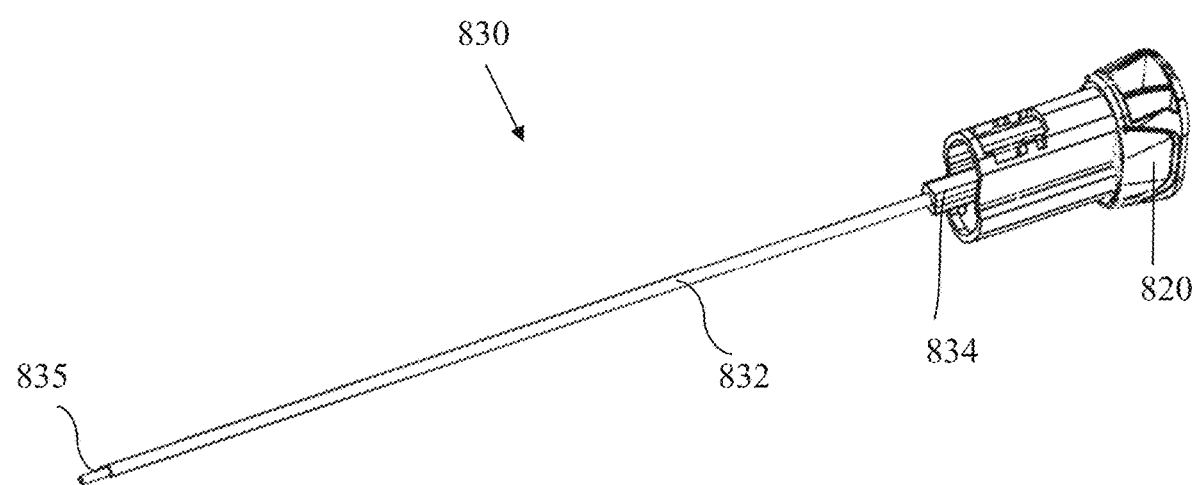
FIG. 68 is a perspective view of a grip assembly.

FIG. 68 is a perspective view of the grip assembly 830. As shown, the grip assembly 830 can include a cannulated tube 832 that includes a cutout portion defining a notch 835 at one end of the tube 832, a retainer 834, and the grip 820. The rod 836 can be integrally defined with the grip 820 via overmolding or another technique and is covered and not visible in FIG. 68. The notch 835 can be used to retain the medial button 850 that can be press fit into the notch 835. The retainer 834 can be force fit over an end of the rod 836 or integrally defined with the grip 820 and the rod 836. The retainer 834 can include geometric features used to mate with and be secured by features of inner portions of the handle 810 and the locking button 815. The rod 836 fits into a lumen or bore of the tube 832 and extends from an end of the tube 832 and is moveable with respect to the tube 832.

Figure 69:
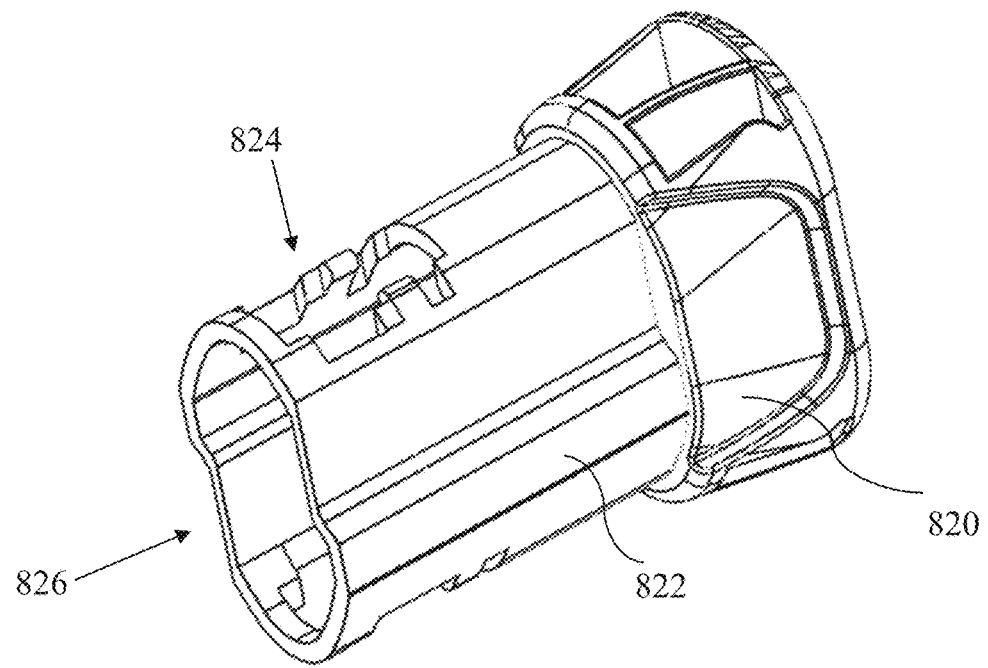
FIG. 69 is a perspective view of a grip.

FIG. 69 is a perspective view of the grip 820. As shown, the grip 820 can include a rounded or oval shaped body 822 configured to fit with the handle 810 and a larger rounded portion at one (the gripping) end. A first opening 824 can be provided through the circumference of the body 822 with a geometric outline to accept the locking button 815. The body 822 can include a second opening 826 at an end opposite to the gripping end to accept the retainer 834 and rod 836.

Figure 70:
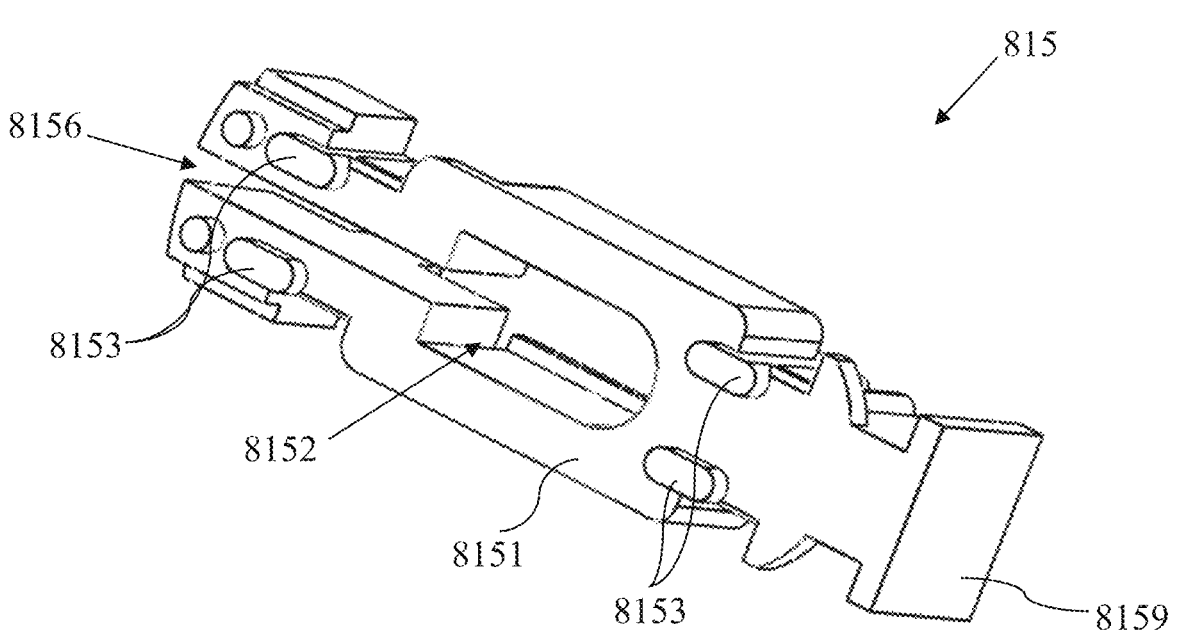
FIG. 70 and FIG. 71 are perspective views of a locking button.
Figure 71:
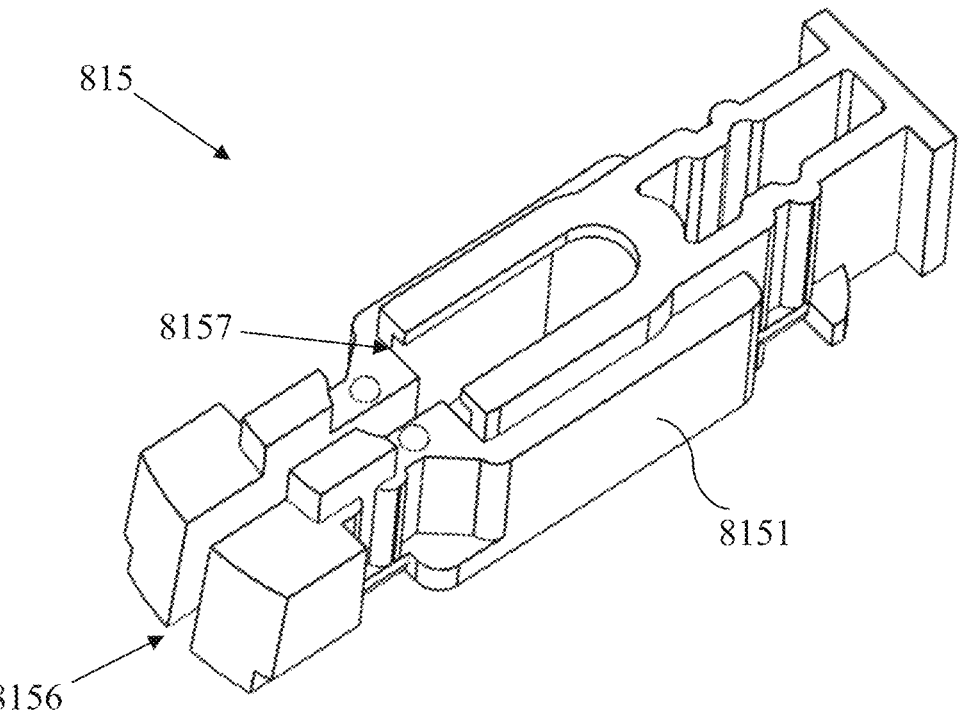

FIGS. 70 and 71 are perspective views of the locking button 815. The locking button 815 can include a body 8151 with an opening 8152 therethrough. Geometric features of the body 8151 defining the opening 8152 permit the rod 836, the tube 832, and the retainer 834 of the grip assembly 830 to fit through the opening 8152. The body 8151 can also include a slot 8156 extending through the body 8151 from one end to the opening 8152 to fit over the rod 836 and the tube 832 to permit the locking button 815 to be moved with respect to the grip assembly 830.

One side of the body 8151 can include two pairs of opposing stops 8153 extending from the body 8151 and used to physically limit movement of the locking button 815 with respect the grip 820. The opposite side of the body 8151 can include a retainer groove 8157 to fit over a flange of the retainer 834 to secure the locking button 815 and the retainer 834 together. A surface 8159 at one end of the locking button 815 can be used to push on the locking button 815 while assembled in the syndesmosis device inserter 800 to unlock the grip assembly 830 to be removable.

Figure 72:
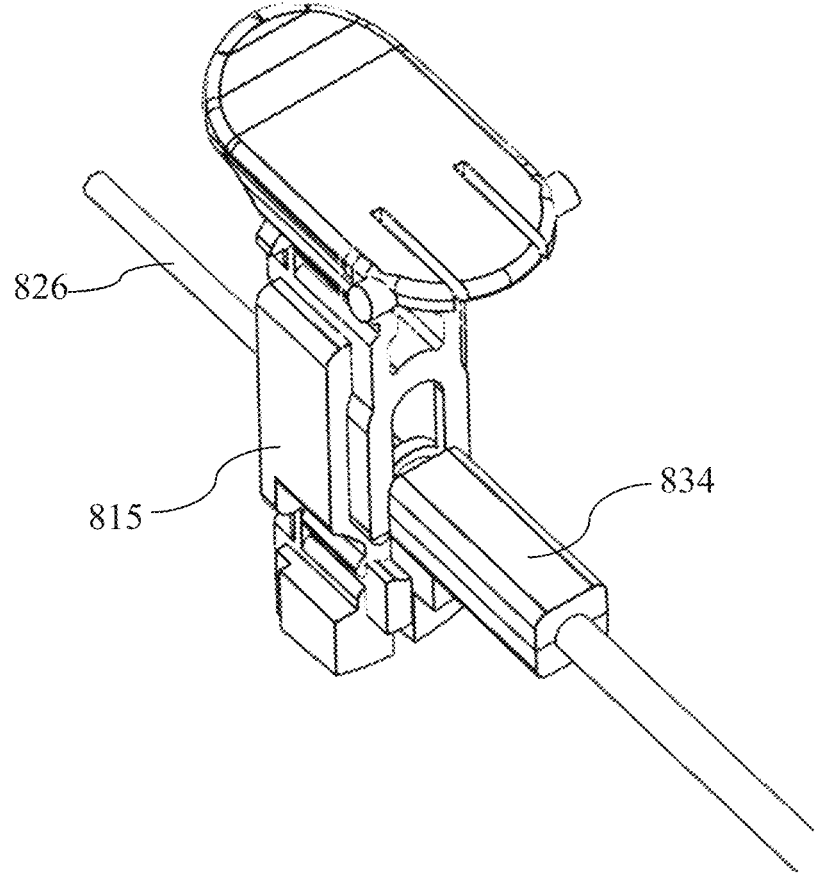
FIG. 72 is a perspective view of an arrangement of a locking button and a retainer.

FIG. 72 is a perspective view of an internal arrangement showing the locking button 815 engaged with the retainer 834.

In operation, with this embodiment of syndesmosis device inserter 800, one end of a suture can be wrapped around and/or tied to one half 810A/810B of the handle 810 within the corresponding suture groove 870A/870B, through the lateral button 840, out of the handle 810 through a corresponding suture hole 818, along the rod 826, through the medial button 850, back along the rod 826, into the handle 810 through the other suture hole 818, through the lateral button 840, and then secured to the other half 810A/810B of the handle 810 within the other corresponding suture groove 870A/870B.

Similar to operation previously described with other embodiments, the syndesmosis device inserter 800 can be gripped with one hand during use. The index and middle finger of one hand can be located for leverage around the finger grips 811A and 811B. The thumb can lift up the safety cover 817 and push down on the surface 8159 of the locking button 815 to release the grip assembly 830 and the grip 820 can be pushed with the palm to release the medial button 840 from the notch 835. After the medial button 840 has been released, the grip assembly 830 can be pulled out of the handle 810 and the two 810A and 810B of the handle 810 can be separated and used to tension the suture and buttons as previously described.

Figure 73:
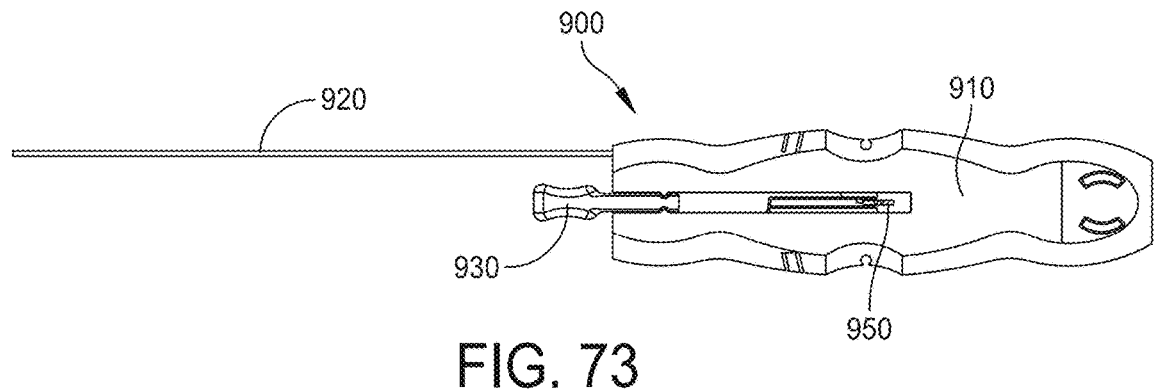
FIG. 73 is a side view of a syndesmosis device inserter according to another embodiment of the present disclosure.
Figure 74:
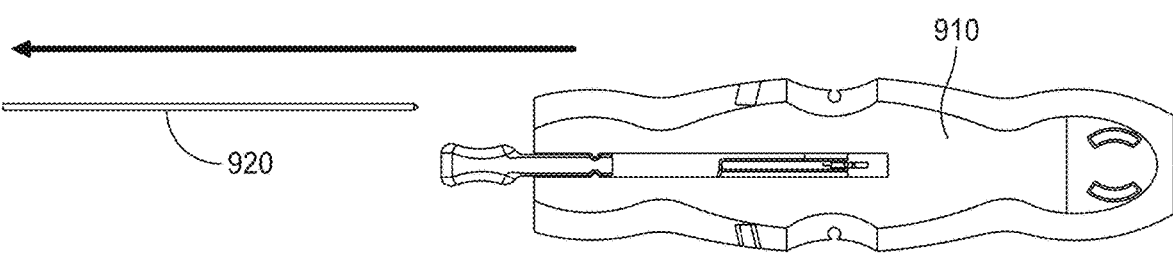
FIG. 74 to FIG. 77 show how a syndesmosis device inserter can be used during a surgical technique.

FIG. 73 is a side view of a knotless syndesmosis device inserter 900 according to another embodiment of the current disclosure. FIG. 73 shows that the knotless syndesmosis device inserter 900 can include a handle 910, a guide wire 920, and a button holder 930 to hold a medial button 950. A knotless lateral button and suture are internal to the handle 910, attached to the guide wire 920, and not visible in the figures.

Figure 75:
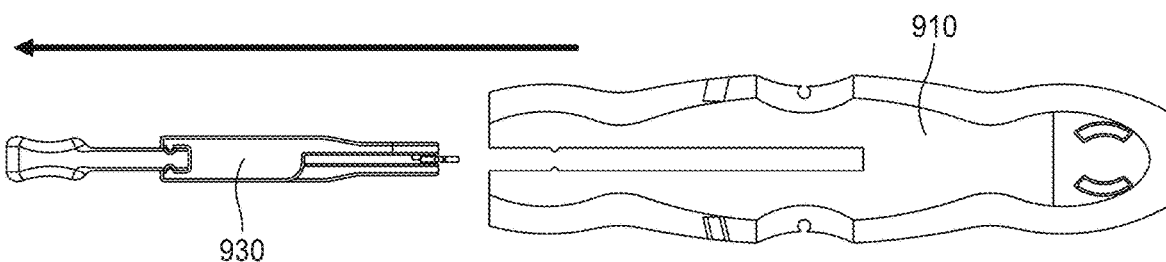
Figure 76:
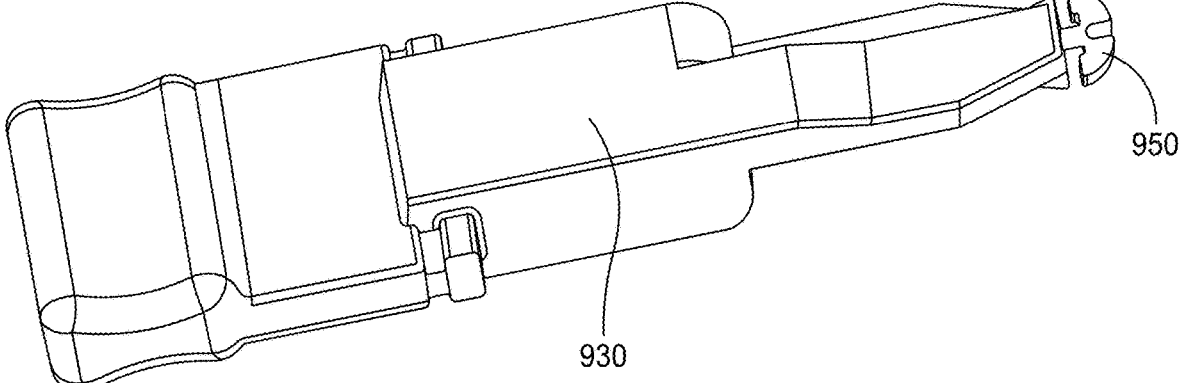
Figure 77:
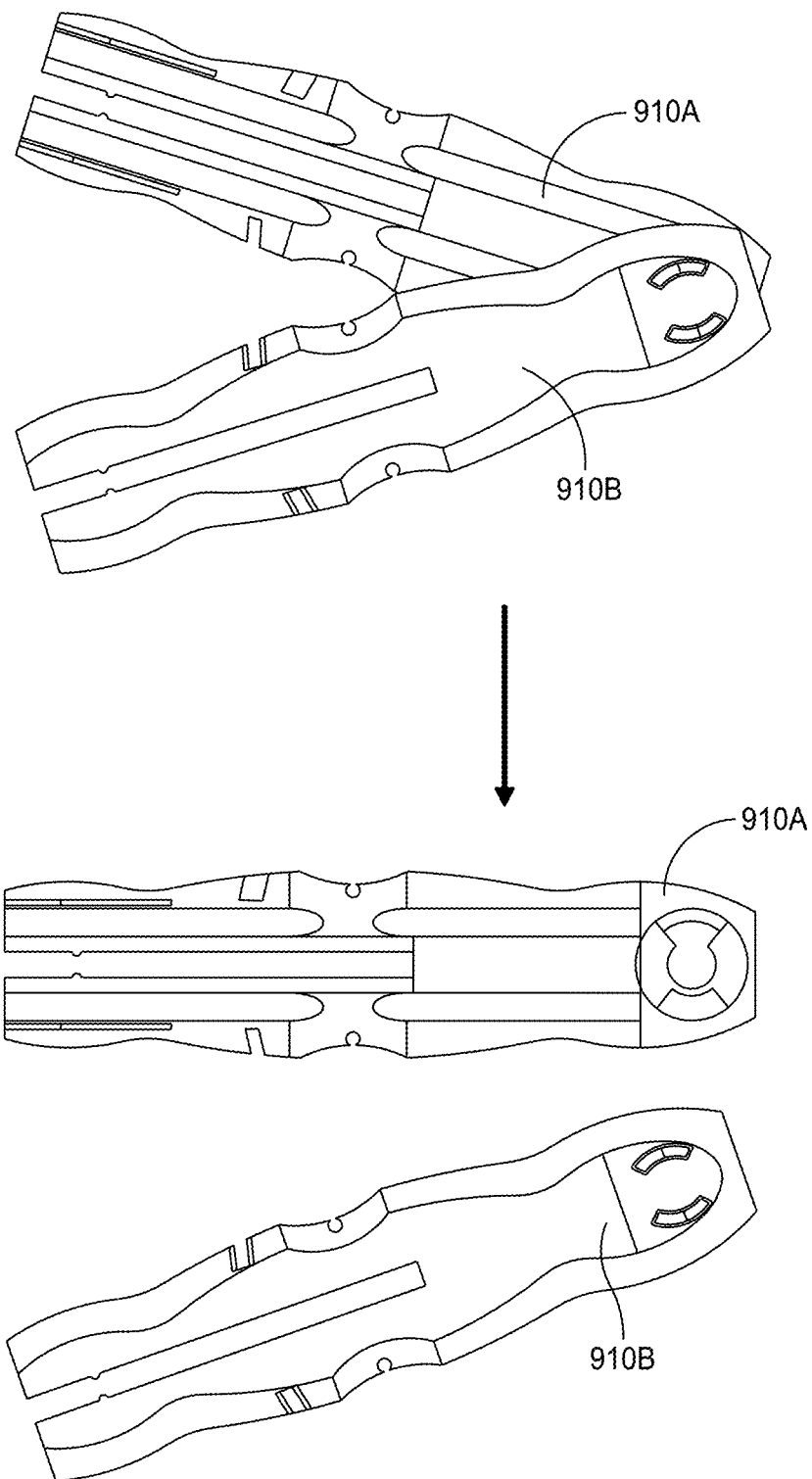

FIGS. 74-77 are used to describe how the knotless syndesmosis device inserter 900 is used. After pilot holes have been drilled through the fibula and the tibia, the guide wire 920 and suture are passed through the pilot holes until a suture loop is visible beyond the farthest bone cortex. During this step shown in FIG. 74, the suture is disconnected from the guide wire 920 and the guide wire 920 is discarded. FIG. 75 shows that the button holder 930 can be separated from the handle 910. FIG. 76 shows the button holder 930 separated from the handle 910. The button holder 930 is used to wrap the suture loop around a central post of the medial button 950. As shown in FIG. 77 two halves 910A and 910B of the handle 910 can be rotated with respect to each other and separated to release the enclosed lateral button (not shown). Each half 910A and 910B of the handle 910 can be used to provide tension to the suture and draw the medial button 950 and lateral button together to fully seat the buttons. The handle halves 910A and 910B can be used to provide final tensioning and knotting of the suture.

It should be understood that the foregoing description is only illustrative of the present invention. Various alternatives and modifications can be devised by those skilled in the art without departing from the present invention. Accordingly, the present invention is intended to embrace all such alternatives, modifications, and variances that fall within the scope of the appended claims.

What is claimed is:

1. A syndesmosis device inserter system comprising:
a handle;
a pusher assembly fit with the handle and including a body, a tube that is cannulated, and a rod attached to the body and fit into the tube; and
a suture secured at a first end to a first half of the handle, threaded through a lateral button located in a groove of the handle and a medial button located at an end of the tube, and secured at a second end to a second half of the handle, wherein the handle is configured such that the first half and the second half are rotatable relative to each other to separate the two halves and release the lateral button from the groove of the handle.

2. The system of claim 1, further comprising a locking button to lock and unlock the pusher assembly from the handle.

3. The system of claim 2, wherein
in a locked state, the locking button prevents the pusher assembly from moving with respect to the handle, and
in an unlocked state, the locking button permits the pusher assembly to move with respect to the handle and push the medial button away from the tube.

4. The system of claim 2, wherein in an unlocked state, the body is configured to move with respect to the handle to force the rod down the tube and push the medial button from the tube.

5. The system of claim 1, wherein the first half and the second half are identical.

6. The system of claim 1, wherein the medial button is oblong and secured into a notch of the tube in an axial alignment.

7. The system of claim 1, wherein the first half and the second half are configured to provide tension to pull the first end and the second end.

8. A syndesmosis device inserter system comprising:
a handle;
a pusher assembly fit with the handle and including a body, a tube that is cannulated, and a rod attached to the body and fit into the tube wherein the body includes an extending portion that includes two release tabs and a claw configured to couple to a retainer attached to the rod; and
a suture secured at a first end to a first half of the handle, threaded through a lateral button located in a groove of the handle and a medial button located at an end of the tube, and secured at a second end to a second half of the handle.

* * * * *